(12) United States Patent
Lau et al.

(10) Patent No.: US 7,976,454 B2
(45) Date of Patent: Jul. 12, 2011

(54) CARDIAC HARNESS

(75) Inventors: Lilip Lau, Los Altos, CA (US); Anuja Patel, Sunnyvale, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 1353 days.

(21) Appl. No.: 11/511,091

(22) Filed: Aug. 28, 2006

(65) Prior Publication Data

US 2007/0021652 A1    Jan. 25, 2007

Related U.S. Application Data

(60) Division of application No. 11/272,566, filed on Nov. 9, 2005, now Pat. No. 7,097,613, which is a continuation-in-part of application No. 10/338,934, filed on Jan. 7, 2003, now Pat. No. 7,174,896.

(60) Provisional application No. 60/346,788, filed on Jan. 7, 2002.

(51) Int. Cl.
 *A61F 2/00* (2006.01)
(52) U.S. Cl. ......................................................... 600/37
(58) Field of Classification Search .............. 600/16–18, 600/37; 128/897, 898; 606/193, 195, 202
See application file for complete search history.

(56) References Cited

U.S. PATENT DOCUMENTS

| 1,682,119 | A | 8/1928 | Field |
|---|---|---|---|
| 2,278,926 | A | 4/1942 | Hartwell |
| 2,826,193 | A | 3/1958 | Vineberg |
| 3,464,322 | A | 9/1969 | Pequignot |
| 3,513,836 | A | 5/1970 | Sausse |
| 3,587,567 | A | 6/1971 | Schiff |
| 3,613,672 | A | 10/1971 | Schiff |
| 3,966,401 | A | 6/1976 | Hancock et al. |
| 3,983,863 | A | 10/1976 | Janke et al. |
| 3,988,782 | A | 11/1976 | Dardik et al. |
| 4,011,947 | A | 3/1977 | Sawyer |
| 4,048,990 | A | 9/1977 | Goetz |
| 4,065,816 | A | 1/1978 | Sawyer |
| 4,108,161 | A | 8/1978 | Samuels et al. |
| 4,192,293 | A | 3/1980 | Asrican |
| 4,211,325 | A | 7/1980 | Wright |
| 4,261,342 | A | 4/1981 | Aranguren Duo |
| 4,306,318 | A | 12/1981 | Mano et al. |

(Continued)

FOREIGN PATENT DOCUMENTS

DE    3831 540 A1    4/1989

(Continued)

OTHER PUBLICATIONS

Bencini, Adriano, M.D., *The "Pneumomassage" of the Heart*, Surgery, vol. 39, No. 3, Mar. 1956.

(Continued)

*Primary Examiner* — Samuel G Gilbert
(74) *Attorney, Agent, or Firm* — Fulwider Patton LLP

(57) ABSTRACT

A cardiac harness for treating or preventing congestive heart failure is configured to be placed about at least a portion of a patient's heart so as to apply a mild compressive force on the heart. In one embodiment, the cardiac harness is configured so that the variation of load as a function of expansion through a selected range of expansion is represented generally in the form y=ax+b, and the value of "a" does not increase as the percent expansion increases.

12 Claims, 17 Drawing Sheets

U.S. PATENT DOCUMENTS

| | | |
|---|---|---|
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |
| 4,545,783 A | 10/1985 | Vaughan |
| 4,628,937 A | 12/1986 | Hess et al. |
| 4,630,597 A | 12/1986 | Kantrowitz et al. |
| 4,665,906 A | 5/1987 | Jervis |
| 4,690,134 A | 9/1987 | Snyders |
| 4,697,703 A | 10/1987 | Will |
| 4,750,619 A | 6/1988 | Cohen et al. |
| 4,821,723 A | 4/1989 | Baker, Jr. et al. |
| 4,827,932 A | 5/1989 | Ideker et al. |
| 4,834,707 A | 5/1989 | Evans |
| 4,838,288 A | 6/1989 | Wright et al. |
| 4,840,626 A | 6/1989 | Linsky et al. |
| 4,863,016 A | 9/1989 | Fong et al. |
| 4,878,890 A | 11/1989 | Bilweis |
| 4,936,857 A | 6/1990 | Kulik |
| 4,957,477 A | 9/1990 | Lundback |
| 4,960,424 A | 10/1990 | Grooters |
| 4,973,300 A | 11/1990 | Wright |
| 4,976,730 A | 12/1990 | Kwan-Gett |
| 5,031,762 A | 7/1991 | Heacox |
| 5,057,117 A | 10/1991 | Atweh |
| 5,067,957 A | 11/1991 | Jervis |
| 5,087,243 A | 2/1992 | Avitall |
| 5,098,369 A | 3/1992 | Heilman et al. |
| 5,106,386 A | 4/1992 | Isner et al. |
| 5,119,804 A | 6/1992 | Anstadt |
| 5,131,905 A | 7/1992 | Grooters |
| 5,150,706 A | 9/1992 | Cox et al. |
| 5,169,381 A | 12/1992 | Snyders |
| 5,186,711 A | 2/1993 | Epstein |
| 5,190,546 A | 3/1993 | Jervis |
| 5,192,314 A | 3/1993 | Daskalakis |
| 5,197,978 A | 3/1993 | Hess |
| 5,256,132 A | 10/1993 | Snyders |
| 5,279,539 A | 1/1994 | Bohan et al. |
| 5,290,217 A | 3/1994 | Campos |
| 5,333,624 A | 8/1994 | Tovey |
| 5,336,254 A | 8/1994 | Brennen et al. |
| 5,344,442 A | 9/1994 | Deac |
| 5,352,184 A | 10/1994 | Goldberg et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,385,229 A | 1/1995 | Bittmann et al. |
| 5,385,528 A | 1/1995 | Wilk |
| 5,405,360 A | 4/1995 | Tovey |
| 5,429,584 A | 7/1995 | Chiu |
| 5,433,727 A | 7/1995 | Sideris |
| 5,456,711 A | 10/1995 | Hudson |
| 5,460,962 A | 10/1995 | Kemp |
| 5,500,015 A | 3/1996 | Deac |
| 5,507,779 A | 4/1996 | Altman |
| 5,509,428 A | 4/1996 | Dunlop |
| 5,524,633 A | 6/1996 | Heaven et al. |
| 5,533,958 A | 7/1996 | Wilk |
| 5,534,024 A | 7/1996 | Rogers et al. |
| 5,545,210 A | 8/1996 | Hess et al. |
| 5,558,617 A | 9/1996 | Heilman et al. |
| 5,571,215 A | 11/1996 | Sterman et al. |
| 5,582,616 A | 12/1996 | Bolduc et al. |
| 5,584,803 A | 12/1996 | Stevens et al. |
| 5,593,424 A | 1/1997 | Northrup III |
| 5,593,441 A | 1/1997 | Lichtenstein et al. |
| 5,597,378 A | 1/1997 | Jervis |
| 5,603,337 A | 2/1997 | Jarvik |
| 5,607,477 A | 3/1997 | Schindler et al. |
| 5,647,372 A | 7/1997 | Tovey et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,727,569 A | 3/1998 | Benetti et al. |
| 5,749,839 A | 5/1998 | Kovacs |
| 5,782,746 A | 7/1998 | Wright |
| 5,800,334 A | 9/1998 | Wilk |
| 5,800,528 A | 9/1998 | Lederman et al. |
| 5,814,097 A | 9/1998 | Sterman et al. |
| 5,824,028 A | 10/1998 | Knisley |
| 5,836,311 A | 11/1998 | Borst et al. |
| 5,848,962 A | 12/1998 | Feindt et al. |
| 5,849,005 A | 12/1998 | Garrison et al. |
| 5,853,422 A | 12/1998 | Huebsch et al. |
| 5,855,601 A | 1/1999 | Bessler et al. |
| 5,865,791 A | 2/1999 | Whayne et al. |
| 5,876,432 A | 3/1999 | Lau et al. |
| 5,904,690 A | 5/1999 | Middleman et al. |
| 5,910,124 A | 6/1999 | Rubin |
| 5,927,284 A | 7/1999 | Borst et al. |
| 5,948,019 A | 9/1999 | Shu et al. |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,007,486 A | 12/1999 | Hunt et al. |
| 6,015,378 A | 1/2000 | Borst et al. |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,110,100 A | 8/2000 | Talpade |
| 6,117,159 A | 9/2000 | Huebsch et al. |
| 6,117,979 A | 9/2000 | Hendriks et al. |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,166,184 A | 12/2000 | Hendriks et al. |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,192,280 B1 | 2/2001 | Sommer et al. |
| 6,193,648 B1 | 2/2001 | Krueger |
| 6,206,820 B1 | 3/2001 | Kazi et al. |
| 6,214,047 B1 | 4/2001 | Melvin |
| 6,217,894 B1 | 4/2001 | Sawhney et al. |
| 6,221,103 B1 | 4/2001 | Melvin |
| 6,224,540 B1 | 5/2001 | Lederman et al. |
| 6,230,714 B1 | 5/2001 | Alferness et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,282,445 B1 | 8/2001 | Reinhardt et al. |
| 6,287,250 B1 | 9/2001 | Peng et al. |
| 6,293,906 B1 | 9/2001 | Vanden Hoek et al. |
| 6,306,141 B1 | 10/2001 | Jervis |
| 6,312,725 B1 | 11/2001 | Wallace et al. |
| 6,352,710 B2 | 3/2002 | Sawhney et al. |
| 6,360,749 B1 | 3/2002 | Jayaraman |
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |

| | | |
|---|---|---|
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B2 | 4/2003 | Alferness |
| 6,547,716 B1 | 4/2003 | Milbocker |
| 6,547,821 B1 | 4/2003 | Taylor et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,620,095 B2 | 9/2003 | Taheri |
| 6,633,780 B1 | 10/2003 | Berger |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,699,259 B2 | 3/2004 | Fogarty et al. |
| 6,701,929 B2 | 3/2004 | Hussein |
| 6,702,732 B1 | 3/2004 | Lau et al. |
| 6,723,041 B2 | 4/2004 | Lau et al. |
| 6,730,016 B1 | 5/2004 | Walsh et al. |
| 6,755,779 B2 | 6/2004 | Vanden Hoek et al. |
| 6,759,431 B2 | 7/2004 | Hunter et al. |
| 6,818,018 B1 | 11/2004 | Sawhney |
| 6,833,408 B2 | 12/2004 | Sehl et al. |
| 6,876,887 B2 | 4/2005 | Okuzumi |
| 6,881,185 B2 | 4/2005 | Vanden Hock et al. |
| 6,887,192 B1 | 5/2005 | Whayne et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 7,022,063 B2 * | 4/2006 | Lau et al. ............... 600/37 |
| 7,077,802 B2 | 7/2006 | Lau et al. |
| 7,081,086 B2 | 7/2006 | Lau et al. |
| 7,097,613 B2 * | 8/2006 | Lau et al. ............... 600/37 |
| 7,291,105 B2 * | 11/2007 | Lau et al. ............... 600/37 |
| 2001/0029314 A1 | 10/2001 | Alferness et al. |
| 2001/0047122 A1 | 11/2001 | Vanden Hoek et al. |
| 2002/0007216 A1 | 1/2002 | Melvin |
| 2002/0022880 A1 | 2/2002 | Melvin |
| 2002/0028981 A1 | 3/2002 | Lau et al. |
| 2002/0052538 A1 | 5/2002 | Lau et al. |
| 2002/0068849 A1 | 6/2002 | Schweich, Jr. et al. |
| 2002/0077524 A1 | 6/2002 | Schweich, Jr. et al. |
| 2002/0077637 A1 | 6/2002 | Vargas et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2003/0004547 A1 | 1/2003 | Owen et al. |
| 2003/0023296 A1 | 1/2003 | Osypka |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0065248 A1 | 4/2003 | Lau et al. |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0102804 A1 | 5/2004 | Chin |
| 2004/0106848 A1 | 6/2004 | Lau et al. |
| 2004/0122069 A1 | 6/2004 | Glombik et al. |
| 2004/0171907 A1 | 9/2004 | Alferness et al. |
| 2004/0171908 A1 | 9/2004 | Alferness et al. |
| 2004/0210104 A1 | 10/2004 | Lau et al. |
| 2004/0230091 A1 | 11/2004 | Lau et al. |
| 2005/0033322 A1 | 2/2005 | Lau et al. |
| 2005/0049611 A1 | 3/2005 | Lau et al. |
| 2005/0055032 A1 | 3/2005 | Lau et al. |
| 2005/0059854 A1 | 3/2005 | Hoek et al. |
| 2005/0059855 A1 | 3/2005 | Lau et al. |
| 2005/0085688 A1 | 4/2005 | Girard et al. |
| 2005/0090707 A1 | 4/2005 | Lau et al. |
| 2005/0102010 A1 | 5/2005 | Lau et al. |
| 2005/0102016 A1 | 5/2005 | Lau et al. |
| 2005/0107661 A1 | 5/2005 | Lau et al. |
| 2005/0119717 A1 | 6/2005 | Lau et al. |
| 2005/0137673 A1 | 6/2005 | Lau et al. |
| 2005/0169958 A1 | 8/2005 | Hunter et al. |
| 2005/0169959 A1 | 8/2005 | Hunter et al. |
| 2005/0182290 A1 | 8/2005 | Lau et al. |
| 2005/0256368 A1 | 11/2005 | Klenk et al. |
| 2005/0283042 A1 | 12/2005 | Meyer et al. |

FOREIGN PATENT DOCUMENTS

| | | |
|---|---|---|
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| EP | 0 791 330 A3 | 8/1997 |
| EP | 0 919 193 A1 | 6/1999 |
| FR | 2 527 435 | 12/1983 |
| FR | 2 645 739 | 10/1990 |
| GB | 2 115 287 A | 9/1983 |
| GB | 2 209 678 A | 5/1989 |
| JP | 1-271829 | 10/1989 |
| SU | 3316206/28-13 | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 00/02500 | 1/1999 |
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |
| WO | WO 00/06026 | 2/2000 |
| WO | WO 00/06027 | 2/2000 |
| WO | WO 00/06028 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO/0036995 | 6/2000 |
| WO | WO 00/42919 | 7/2000 |
| WO | WO 00/45735 | 8/2000 |
| WO | WO 00/48795 | 8/2000 |
| WO | WO 00/62727 | 10/2000 |
| WO | WO 00/74769 | 12/2000 |
| WO | WO 01/17437 | 3/2001 |
| WO | WO 01/21098 | 3/2001 |
| WO | WO 01/50981 | 7/2001 |
| WO | WO 01/67985 | 9/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |
| WO | WO 02/13726 | 2/2002 |

| | | |
|---|---|---|
| WO | WO 02/19917 | 3/2002 |
| WO | WO 03/026483 | 4/2003 |
| WO | WO 03/026484 | 4/2003 |
| WO | WO 03/026485 | 4/2003 |

OTHER PUBLICATIONS

Anstadt, George L., et al., *A New Instrument for Prolonged Mechanical Cardiac Massage, Abstracts of the 38th Scientific Sessions*, Supplement II to Circulation, vol. 31 and 32, pp. 375-384, Oct. 1965.

Lev, Maurice, M.D., et al., *Single (Primitive) Ventricle, Circulation*, vol. 39, pp. 577-591.

Paling, D.F., *Warp Knitting Technology*, 1970.

Edie, Richard N., M.D., et al., *Surgical Repair of Single Ventricle, The Journal of Thoracic and Cardiovascular Surgery*, vol. 66, No. 3, pp. 350-360, Sep. 1972.

McGoon, Dwight C., M.D., et al., *Correction of the Univentricular Heart Having Two Atriovantricular Valves, The Journal of Thoracic and Cardiovascular Surgery*, vol. 74, No. 2, pp. 218-226, Aug. 1977.

Doty, Donald B., et al., *Septation of the Univentricular Heart: Transatrial Approach, The Journal of Thoracic and Cardiovascular Surgery*, vol. 78, No. 3, pp. 424-430, Sep. 1979.

Schetky, L. McDonald, *Shape- Memory Alloys, Scientific American*, vol. 241, No. 5, pp. 74-82, Nov. 1979.

Melton, K.N., et al., *Alloys With Two-Shape Memory Effect, Mechanical Engineering*, pp. 42-43, Mar. 1980.

Feldt, Robert H., M.D., et al., *Current Status of the Septation Procedure for Univentricular Heart, The Journal of Thoracic and Cardiovascular Surgery*, vol. 82, No. 1, pp. 93-97, Jul. 1981.

Carpentier, A., et al., *Myocardial Substitution With Stimulated Skeletal Muscle: First Successful Clinical Case, The Lancet*, Jun. 1, 1985.

Anstadt, George L. et al., *Direct Mechanical Ventricular Actuation: A Review, Resuscitation*, pp. 7-23, 1991.

Anstadt, Mark P., M.D., et al., *Pulsatile Reperfusion After Cardiac Arrest Improves Neurologic Outcome, American Surgery*, vol. 214, No. 4, pp. 478-490, Oct. 1991.

Schumacker, Harris B., Jr., *Chapter 21: Cardiac Aneurysms, The Evolution of Cardiac Surgery*, pp. 159-165, 1992.

Savage, Edward B., M.D., et al., *Repair of Left Ventricular Aneurysm, The Journal of Thoracic and Cardiovascular Surgery*, vol. 104, No. 3, pp. 752-762, Sep. 1992.

Carpentier, Alain, M.D., Ph.D., et al., *Dynamic Cardiomyoplasty at Seven Years, The Journal of Thoracic and Cardiovascular Surgery*, vol. 106, No. 1, pp. 42-54, Jul. 1993.

Capouya, Eli R., M.D., et al., *Girdling Effect of Nonstimulated Cardiomyoplasty on Left Ventricular Function, Annals of Thoracic Surgeons*, vol. 56, pp. 867-71, 1993.

Chekanov, Valeri, M.D., Ph.D., *Nonstimulated Cardiomyoplasty Wrap Attenuated the Degree of Left Ventricular Enlargement, Annals of Thoracic Surgeons*, vol. 57, pp. 1684-1690, 1997.

Chiu, Ray C.-J, *Using Skeletal Muscle for Cardiac Assistance, Scientific American*, pp. 68-77, Nov./Dec. 1994.

Kass, David A., M.D., et al., *Reverse Remodeling From Cardiomyoplasty in Human Heart Failure: External Constraint Versus Active Assist, Circulation*, vol. 91, No. 9, pp. 2314-2318, May 1, 1995.

Vaynblat, Mikhail, M.D., et al., *Cardiac Binding in Experimental Heart Failure, Annals of Thoracic Surgery (Abstract)*, Supplement to Circulation, vol. 92, Suppl. 1, 1995.

Levin, Howard R., M.D., et al., *Reversal of Chronic Ventricular Dilation in Patients With End-Stage Cardiomyopathy by Prolonged Mechanical Unloading, Circulation*, vol. 91, No. 11, pp. 2717-2720, 1995.

Chaudhry, Pervaiz A., M.D., et al., *Acute Ventricular Reduction with Acorn's Cardiac Support Device Prevents Progressive Left Ventricular Dysfunction and Remodeling in Dogs With Advanced Heart Failure, Cardiothoracic Surgery*, pp. 146-148, 1996.

Oh, Joong Hwan, M.D., et al., *Mechanisms of Dynamic Cardiomyoplasty: Current Concepts, Journal of Cardiac Surgery*, vol. 11, pp. 194-199, 1996.

Badhwar, Vinay, *Power Generation From Four Skeletal Muscle Configurations Design Implications for a Muscle Powered Cardiac Assist Device, ASAIO Journal*, vol. 43, pp. M654-M657, 1997.

Westaby, Stephen, et al., *Landmarks in Cardiac Surgery*, pp. 198-199, 1997.

Cox, James L., *Left Ventricular Aneurysms: Pathophysiologic Observations and Standard Resection, Seminars in Thoracic and Cardiovascular Surgery*, vol. 9, pp. 113-122, Apr. 1997.

Coletta, C., et al., Prognostic Value of Left Ventricular vol. Response During Dobutamine Stress Echocardiography, European Heart Journal, vol. 18, pp. 1599-1603, Oct. 1997.

Capomolla, Soccorso, M.D., et al., *Dobutamine and Nitroprusside Infusion in Patients With Severe Congestive Heart Failure: Hemodynamic Improvement by Discordant Effects on Mitral Regurgitation, Left Atrial Function, and Ventricular Function, American Heart Journal*, 1089-1098, Dec. 1997.

Oh, Joong Hwan, *The Effects of Prosthetic Cardiac Binding and Adynamic Cardiomyoplasty Cardiomyopathy in a Model of Dilated Cardiomyopathy, The Journal of Thoracic and Cardiovascular Surgery*, vol. 116, No. 1, pp. 148-153, 1998.

Cohn, Jay N., M.D., *Preventing Congestive Heart Failure, American Family Physician*, 6 pages, Apr. 15, 1998.

Cohn, Jay N., M.D., *Structural Basis for Heart Failure: Ventricular Remodeling and Its Pharmacological Inhibition, Circulation*, vol. 91, No. 10, pp. 2504-2507, May 15, 1995.

Gaudron, Peter, M.D., et al., *Progressive Left Ventricular Dysfunction and Remodeling After Myocardial Infarction, Circulation*, vol. 87, pp. 755-763, Mar. 1993.

Pfeffer, Marc A., M.D., et al., *Ventricular Remodeling After Myocardial Infarction: Experimental Observations and Clinical Implications, Circulation*, vol. 81, No. 4, pp. 1161-1172, Apr. 1990.

Guasp, Francisco Torrent, *Una protesis contentiva para el tratamiento de le microcardiopatia dilatads, Revista Española de Cardiologia*, vol. 51, No. 7, Jul. 1998.

Power, J.M., et al., *Passive Ventricular Constraint Amends the Course of Heart Failure: A Study in an Ovine Model of Dilated Cardiomyopathy, Cardiovasuclar Research*, vol. 44, pp. 549-555, 1999.

Frazier, O.H., M.D., et al., *Left Ventricular Assist System as a Bridge to Myocardial Recovery, Annals of Thoracic Surgery*, vol. 68, pp. 734-741, 1999.

Melvin, David B., *Ventricular Radius Reduction Without Resection: A Computational Analysis, ASAIO Journal*, pp. 160-165, 1999.

Abstracts—Heart Failure, JACC Feb. 1999.

Raman, Jai S., Fracs, et al., Ventricular Containment as an Adjunctive Procedure in Ischemic Cardiomyopathy: Early Results, Annals of Thoracic Surgery, vol. 70, pp. 1124-1126, Jan. 2000.

McCarthy, Patrick M., et al., *Device Based Left Ventricular Shape Change Immediately Reduces Left Ventricular Volume and Increases Ejection Fraction in a Pacing Induced Cardiomyopathy Model in Dogs*, JACC, Feb. 2000.

Chaudhry, Pervaiz A., M.D., et al., *Passive Epicardial Containment Prevents Ventricular Remodeling in Heart Failure, Annals of Thoracic Surgeons*, vol. 70, pp. 1275-1280, 2000.

Acorn Cardiovascular, Inc., *CSD Specifications Acorn Cardiac Support Device*, 2000.

Heart "jacket" could help stop heart failure progression. Clinicia, No. 916, Jul. 2000.

Acorn Cardiovascular, Inc., *CorCap™ Cardiac Support Device Pamphlet*, Jun. 2001.

Medtronic's InSync Cardiac Resynchronization Therapy Device Approved by FDA, (Press Release) Aug. 28, 2001.

Oz, Mehmet C., M.D., *Passive Ventricular Constraint for the Treatment of Congestive Heart Failure, Annals of Thoracic Surgery*, vol. 71, pp. 5185-5187, 2001.

Abstract Supplement, European Heart Journal, vol. 22, Sep. 2001.

Gorman, J., *Self-Sutures: New Material Knots Up on Its Own, Science News*, vol. 161, p. 262, Apr. 27, 2002.

Teckell-Taylor, Leah A., *Passive Ventricular Restaint With Nitinol Mesh Attenuates Remodeling Following Acute Myocardial Infarction*, Abstract, American College of Cardiology (Undated).

Mann, Douglas L., M.D., *Basic Mechanisms of Remodeling and Reverse Remodeling*, presented at 6th Annual Scientific Meeting of the Heart Failure Society of America, Sep. 24, 2002.

Bocchi, Edimar a., M.D., *Arrhythmias and Suddent Death After Dynamic Cardiomyoplasty, Circulation,* vol. 90, No. 5, Part 2, pp. 11-107 thru 11-111, Nov. 1994.

Chachques, Juan C., M.D., *Study of Muscular and Ventricular Function in Dynamic Cardiomyoplasty: A Ten-Year Follow-Up, The Journal of Heart and Lung Transplantation,* vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart,* The Heart Surgery Forum, #2001-1818, pp. 361-363, Jan. 4-7, 2001.

Macris, Michael P. M.D., et al., *Minimally Invasive Access of the Normal Preicardium: Initial Clinical Experience with a Novel Device, Clinical Cardiology,* vol. 22 (Suppl. 1), pp. 1-36 thru 1-39, 1999.

Thakur, Ranjan K., M.D., et al., *Latissimus Dorsi Dynamic Cardiomyoplasty: Role of Combined ICD Implantation, Journal of Cardiac Surgery,* vol. 10, pp. 295-297, 1995.

Wharton, J. Marcus, et al., *Electrophysiological Effects of Monophasic and Biphasic Stimuli in Normal and Infarcted Dogs, PACE,* vol. 13, pp. 1158-1172, Sep. 1990.

Shabetai, Ralph, *The Role of the Pericardium in the Pathophysiology of Heart Failure, Congestive Heart Failure,* Second Edition, Chapter 9, pp. 157-187, 2000.

Cohn, Jay N., M.D., *The Management of Chronic Heart Failure, The New England Journal of Medicine,* vol. 335, No. 7, pp. 490-498, Aug. 15, 1996.

Zhou, Xiaohong, et al., *Epicardial Mapping of Ventricular Defibrillation With Monophasic and Biphasic Shocks in Dogs, Circulation Research,* vol. 72, No. 1, pp. 145-160, Jan. 1993.

Shorofsky, Stephen R., et al., *Comparison of Step-Down and Binary Search Algorithms for Determination of Defibrillation Threshold in Humans, PACE,* vol. 27, pp. 218-220, Feb. 2004.

Gold, Michael R., M.D., et al., *Comparison of Single- and Dual-Coil Active Pectoral Defibrillation Lead Systems, Journal of the American College of Cardiology,* vol. 31, No. 6, pp. 1391-1394, May 1998.

Rinaldi, C. Aldo, *A Randomized Prospective Study of Single Coil Versus DualCoil Defibrillation in Patients With Ventricular Arrhythmias Undergoing Implantable Cardioverter Defibrillator Therapy, PACE,* vol. 26, pp. 1684 1690, Aug. 2003.

Schwartzman, David, M.D., et al., *Serial Defibrillation Lead Impedance in Patients with Epicardial and Nonthoracotomy Lead Systems, Journal of Cardiovascular Electrophysiology,* vol. 7, No. 8, pp. 697-703, Aug. 1996.

Sandstedt, Bengt, et al., *Bidirectioinal Defibrillation Using Implantable Defibrillators: A Prospective Randomized Comparison Between Pectoral and Abdominal Active Generators, PACE,* vol. 24, Part 1, pp. 1343-1353, Sep. 2001.

Schulte, B., et al., *Dual-Coil vs. Single-Coil Active Pectoral Implantable Defibrillator Lead Systems: Defibrillation Lead Requirements and Probability of Defibrillation Success at Multiples of the Defibrillation Energy Requirements, Europace,* vol. 3, pp. 177-180, Jul. 2001.

Application for U.S. Letters U.S. Appl. No. 10/338,934, filed Jan. 7, 2003; Inventor: Lau.

Application for U.S. Letters U.S. Appl. No. 11/343,926, filed Jan. 30, 2006; Inventor: Lau et al.

Application for U.S. Letters U.S. Appl. No. 11/304,070, filed Dec. 14, 2005; Inventor: Lau et al.

Application for U.S. Letter U.S. Appl. No. 11/317,624, filed Dec. 22, 2005; Inventor: Lau et al.

\* cited by examiner ary of U.S. Ser. No. 11/272,566
CARDIAC HARNESS

CROSS-REFERENCES TO RELATED APPLICATIONS

This application is a division of U.S. Ser. No. 11/272,566 filed Nov. 9, 2005 now U.S. Pat. No. 7,097,613 which is a continuation-in-part application of U.S. Ser. No. 10/338,934, filed Jan. 7, 2003 now U.S. Pat. No. 7,174,896 which is based on and claims priority to U.S. Provisional Application No. 60/346,788, filed Jan. 7, 2002. The entirety of each of these applications is hereby incorporated by reference.

BACKGROUND OF THE INVENTION

The present invention relates to a device for treating heart failure. More specifically, the invention relates to a cardiac harness configured to be fit around at least a portion of a patient's heart.

DESCRIPTION OF THE RELATED ART

Congestive heart failure ("CHF") is characterized by the failure of the heart to pump blood at sufficient flow rates to meet the metabolic demand of tissues, especially the demand for oxygen. One characteristic of CHF is remodeling of at least portions of a patient's heart. Remodeling involves physical changes to the size, shape and thickness of the heart wall. For example, a damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. Thus, a vicious cycle can result, in which dilation leads to further dilation and greater functional impairment.

A harness is constructed of polyester filaments knit in a well known "Atlas knit" arrangement, such as that discussed in international patent Publication Number WO 01/95830 A2, which is incorporated herein by reference in its entirety. As such, the harness is flexible, and the fabric can stretch, even though the polyester filaments do not necessarily elastically deform upon stretching of the fabric. Such fabric stretch is mainly due to linearization of filaments and fiber crimp and geometric distortion of the knit pattern. Once these stretch factors are exhausted, the harness becomes inelastic, and will no longer expand elastically with an increase in size of a patient's heart.

With reference to FIG. 13, an anticipated compliance curve charting the compliance of a cardiac harness constructed of a knit material such as a harness constructed employing an "Atlas knit" as discussed above. As shown in the drawing, the curve appears generally parabolic in shape. That is, as the percent tensile strain increases the corresponding load increases exponentially. It is anticipated that an asymptote will be defined at a percent strain between about forty to fifty percent. At that point the limit of expansion will have been reached.

Historically, congestive heart failure has been managed with a variety of drugs. Devices have also been used to improve cardiac output. For example, left ventricular assist pumps help the heart to pump blood. Multi-chamber pacing has also been employed to optimally synchronize the beating of the heart chambers to improve cardiac output. Various skeletal muscles, such as the latissimus dorsi, have been used to assist ventricular pumping. Researchers and cardiac surgeons have also experimented with prosthetic "girdles" disposed around the heart. One such design is a prosthetic "sock" or "jacket" that is wrapped around the heart.

Although some of the above-discussed devices hold promise, there remains a need in the art for an improved device for treating CHF to prevent a remodeled heart from further remodeling and/or help reverse remodeling of a diseased heart.

SUMMARY OF THE INVENTION

In accordance with one embodiment of the present invention, a cardiac harness is configured to fit generally around a patient's heart and to resist expansion of the heart by applying a compressive force thereto. At least a section of said harness exerts a circumferential load, normalized with respect to a longitudinal direction and expressed in pounds per inch, as a function of circumferential expansion of said section of harness, expressed as a percent of expansion above a zero load condition. The harness has an operating range of expansion having a minimum value of at least twenty percent. A change of twenty percent in said circumferential expansion within said operating range yields a change in circumferential load of no more than about 0.116 N/cm (0.066 lbF/in).

In accordance with a further embodiment, the circumferential compliance of the harness over the operating range of expansion is greater than a longitudinal compliance of the harness.

In accordance with another embodiment of the present invention, a cardiac harness is configured to fit generally around a patient's heart and to resist expansion of the heart by applying a compressive force thereto. At least a section of said harness exerts a circumferential load, normalized with respect to a longitudinal direction and expressed in pounds per inch, as a function of circumferential expansion of said section of harness, expressed as a percent of expansion above a zero load condition. The variation of load as a function of expansion through a selected range of expansion is generally in the form of y=ax+b where a and b are determined by linear regression. A first value of "a" corresponds to a first selected range of expansion of at least five percent, and a second value of "a" corresponds to a second selected range of expansion of at least five percent. The second range of expansion consists of values greater than the first range of expansion so as to be nonoverlapping with the first range, and the second value of "a" is no greater than said first value of "a."

In accordance with another embodiment, the present invention provides a cardiac harness configured to fit generally around a patient's heart and to resist expansion of the heart by applying a compressive force thereto. At least a section of said harness exerts a circumferential load, normalized with respect to a longitudinal direction and expressed in pounds per inch, as a function of circumferential expansion of said section of harness, expressed as a percent of expansion above a zero load condition. The variation of load as a function of expansion between twenty percent expansion and thirty percent expansion is generally in the form of y=ax+b where "a" and "b" are determined by linear regression. The linear regression of said variation of load as a function of expansion yields a coefficient of determination of at least about 0.8. The value of "a" is no greater than about 0.0058 N/cm per percent expansion (0.0033 lbF/in per percent expansion.

In another embodiment, the value of "a" is no greater than about 0.0035 N/cm per percent expansion (0.002 lbF/in per percent expansion).

In accordance with still a further embodiment of the present invention, a cardiac harness is configured to fit generally around a patient's heart and to resist expansion of the heart by applying a compressive force thereto. At least a section of said harness exerts a circumferential load, normalized with respect to a longitudinal direction and expressed in pounds per inch, as a function of circumferential expansion of said section of harness, expressed as a percent of expansion above a zero load condition. The variation of load as a function of expansion through a selected range of expansion is generally in the form of $y=cXZ+ax+b$ where c, a and b are determined by linear regression, and c is negative.

Further features and advantages of the present invention will become apparent to one of skill in the art in view of the Detailed Description of Preferred Embodiments which follows, when considered together with the attached drawings and claims.

DETAILED DESCRIPTION OF THE PREFERRED EMBODIMENTS

This application relates to a method and apparatus for treating heart failure. As discussed in Applicants' co-pending application entitled "Expandable Cardiac Harness For Treating Congestive Heart Failure," Ser. No. 09/634,043, which was filed on Aug. 8, 2000, the entirety of which is hereby expressly incorporated by reference herein, it is anticipated that remodeling of a diseased heart can be resisted or even reversed by alleviating the wall stresses in such a heart. The present application discusses certain embodiments and methods for supporting the cardiac wall. Additional embodiments and aspects are also discussed in Applicants' co-pending applications entitled "Cardiac Harness," Ser. No. 10/656,733, filed Sep. 5, 2003, "Device for Treating Heart Failure," Ser. No. 10/242,016, filed Sep. 10, 2002, and "Heart Failure Treatment Device and Method," Ser. No. 10/287,723, filed Oct. 31, 2002, the entirety of each of which are hereby expressly incorporated by reference.

Figure 1:
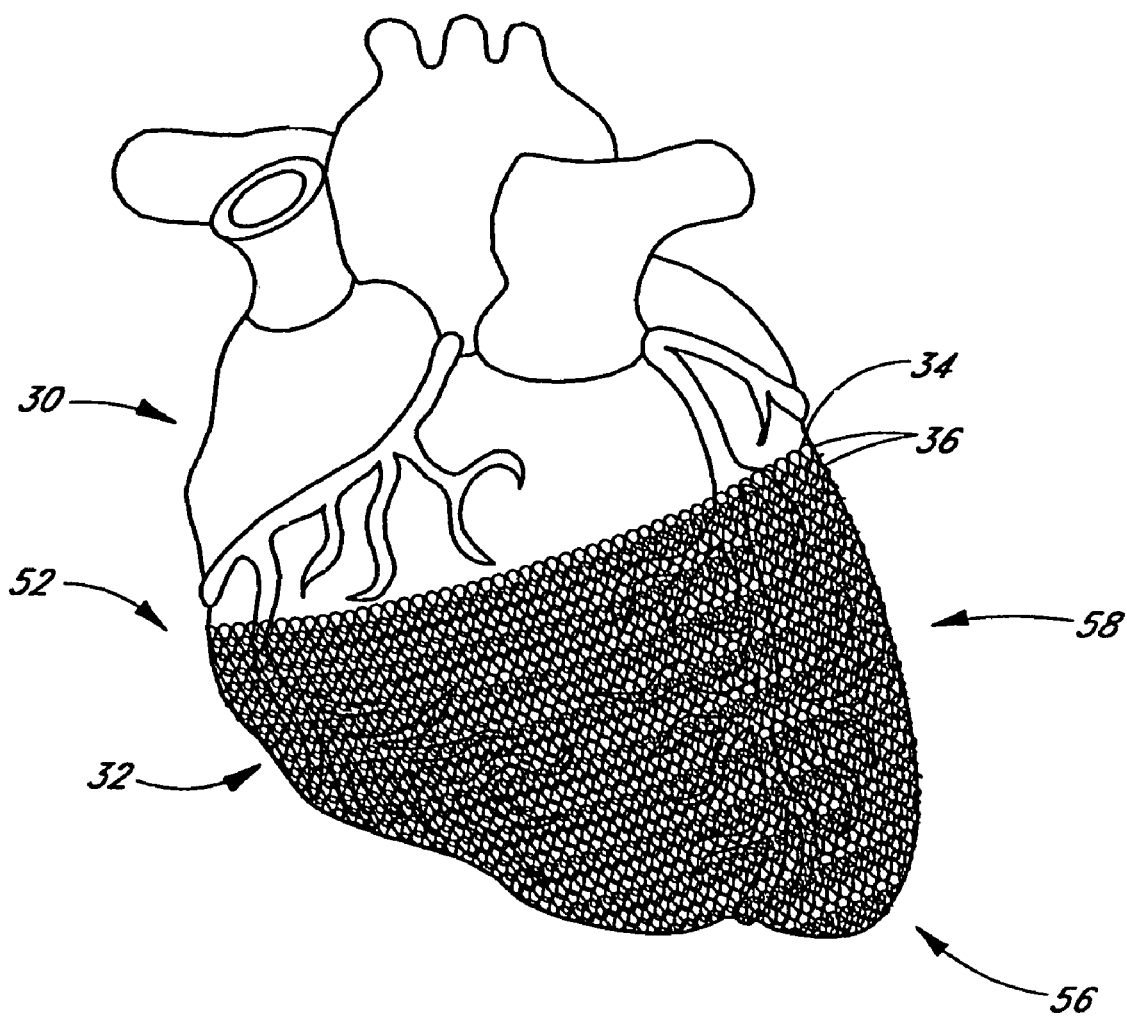
FIG. 1 is a schematic view of a heart with a cardiac harness placed thereon.

FIG. 1 illustrates a mammalian heart 30 having a cardiac wall stress reduction device in the form of a harness 32 applied to it. The cardiac harness 32 comprises a series of hinges or spring elements 34 that circumscribe the heart 30 and, collectively, apply a mild compressive force on the heart so as to alleviate wall stresses.

The term "cardiac harness" as used herein is a broad term that refers to a device fit onto a patient's heart to apply a compressive force on the heart during at least a portion of the cardiac cycle. Other devices that are intended to be fit onto a heart and are referred to in the art as "girdles," "socks," "jackets," or the like are included within the meaning of "cardiac harness."

Figure 2A:
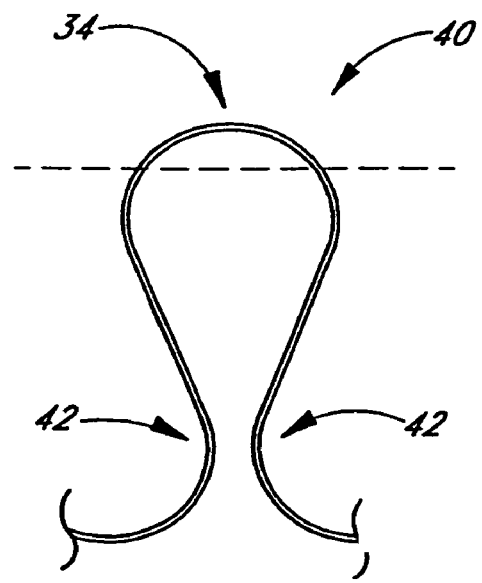
FIGS. 2A-2B illustrate a spring hinge in a relaxed position and under tension.
Figure 2B:
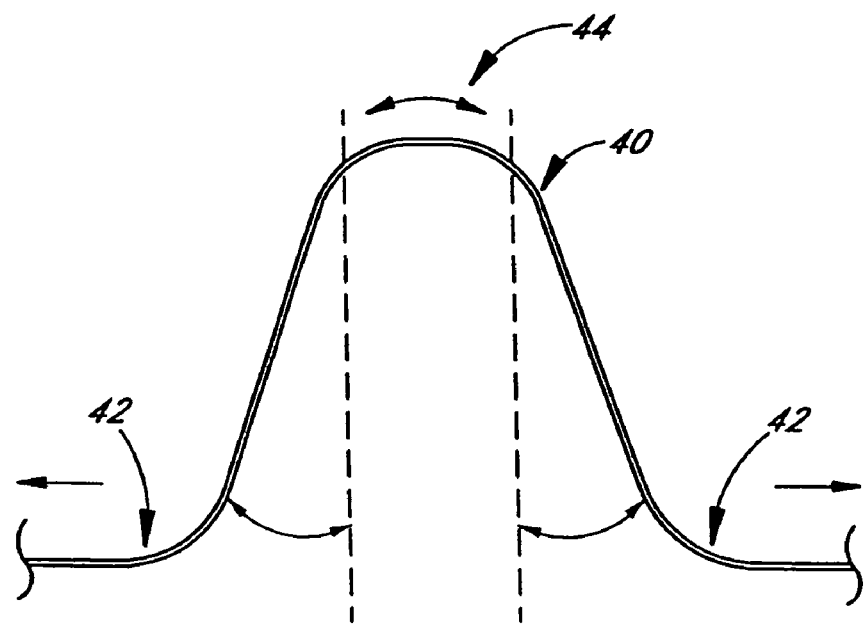

The cardiac harness 32 illustrated in FIG. 1 comprises at least one undulating strand 36 comprising a series of spring elements 34 referred to as hinges or spring hinges that are configured to deform as the heart 30 expands during filling. Each hinge 34 provides substantially unidirectional elasticity, in that it acts in one direction and does not provide much elasticity in the direction perpendicular to that direction. For example, FIG. 2A shows one embodiment of a hinge member 34 at rest. The hinge member 34 has a central portion 40 and a pair of arms 42. As the arms are pulled, as shown in FIG. 2B, a bending moment 44 is imposed on the central portion 40. The bending moment 44 urges the hinge member 34 back to its relaxed condition. Note that a typical strand comprises a series of such hinges, and that the hinges 34 are adapted to elastically expand and retract in the direction of the strand 36.

In the embodiment illustrated in FIG. 1, the strands 36 of spring elements 34 are constructed of extruded wire that is deformed to form the spring elements. Although FIG. 1 shows adjacent strands 36 interwoven one with another, it is to be understood that, in additional embodiments, adjacent strands 36 may not overlay or touch one another.

Figure 3:
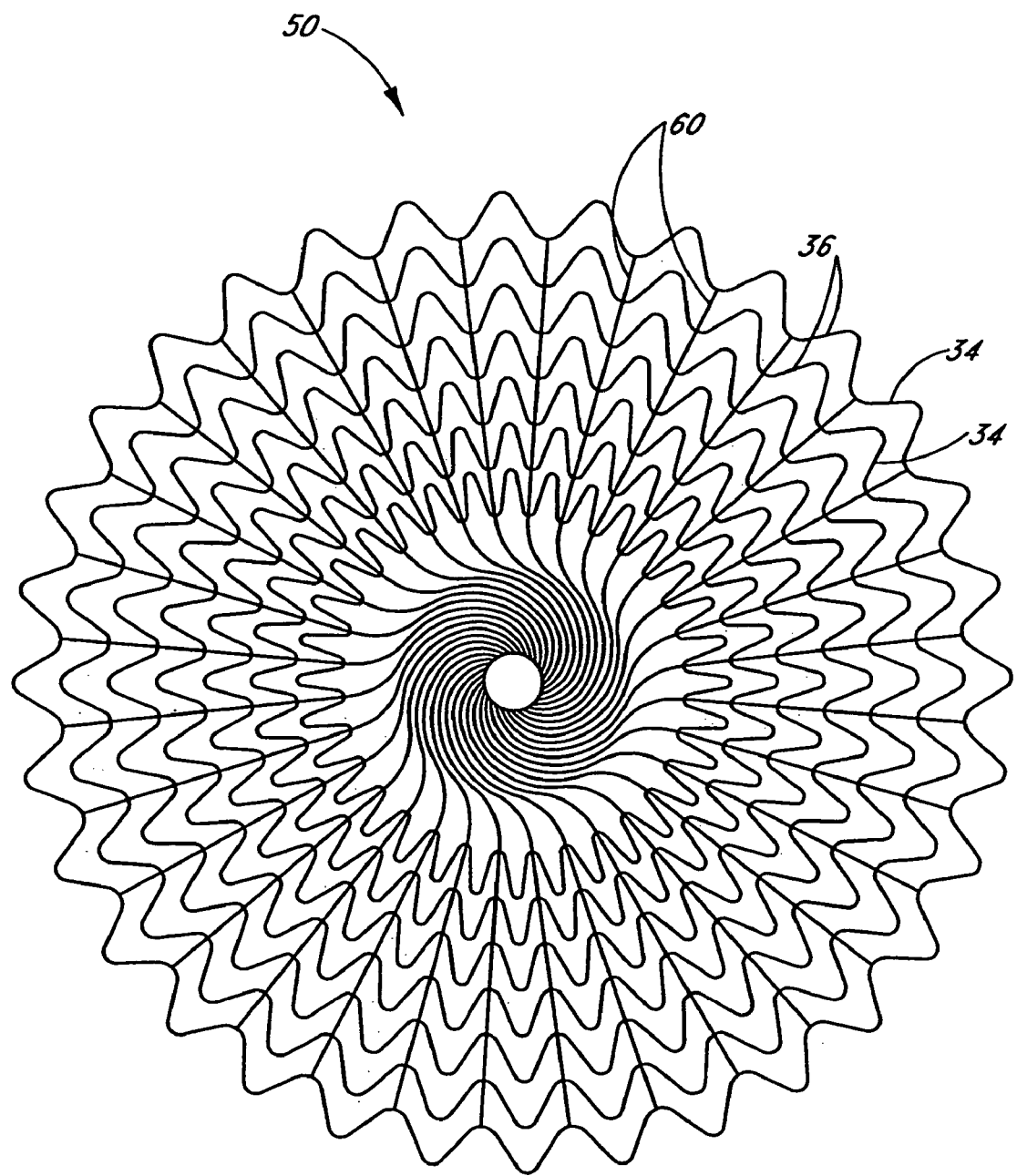
FIG. 3 shows an embodiment of a cardiac harness that has been cut out of a flat sheet of material.
Figure 4:
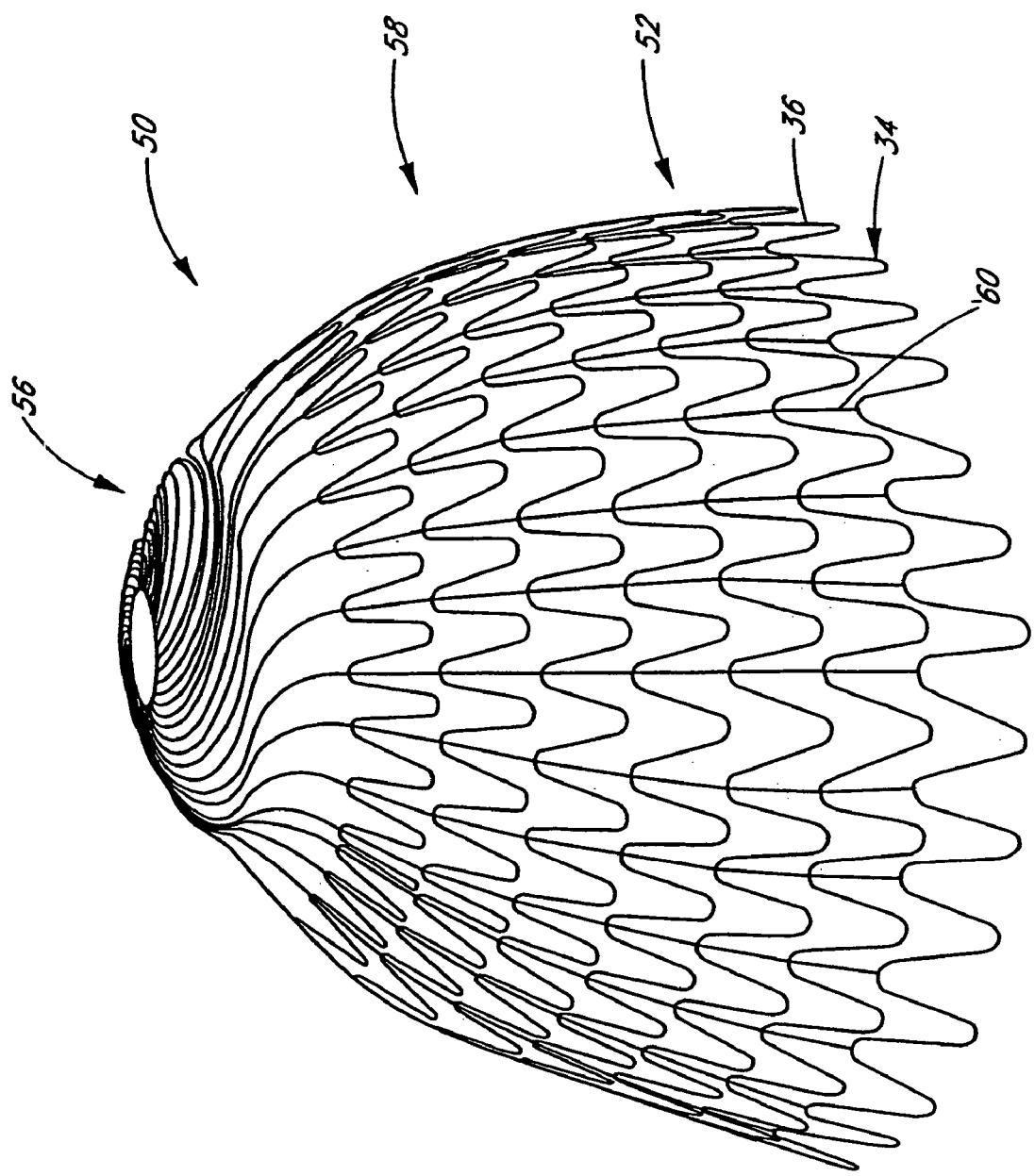
FIG. 4 shows the cardiac harness of FIG. 3 formed into a shape configured to fit about a heart.

FIGS. 3 and 4 illustrate another preferred embodiment of a cardiac harness 50, shown at two points during manufacture of such a harness. In the illustrated embodiment, the harness 50 is first formed from a relatively thin, flat sheet of material. Any method can be used to form the harness from the flat sheet. For example, in one embodiment, the harness is photochemically etched from the material; in another embodiment, the harness is laser-cut from the thin sheet of material. The embodiment shown in FIGS. 3 and 4 has been etched from a thin sheet of Nitinol, which is a superelastic material that also exhibits shape memory properties. The flat sheet of material is draped over a form, die or the like, and is formed to generally take on the shape of at least a portion of a heart.

With reference to FIGS. 1 and 4, the illustrated embodiments of the cardiac harnesses 32,50 comprise a base portion 52, which is sized and configured to generally engage and fit onto a base region of a patient's heart; an apex portion 56, which is sized and shaped so as to generally engage and fit on an apex region of a patient's heart; and a medial portion 58 between the base and apex portions.

In the embodiment shown in FIGS. 3 and 4, the harness 50 comprises strands or rows 36 of undulating wire. As discussed above, the undulations comprise hinges/spring elements 34 which are elastically bendable in a desired direction. Some of the strands 36 are connected to each other by interconnecting elements 60. The interconnecting elements 60 help maintain the position of the strands 36 relative to one another. Preferably the interconnecting elements 60 allow some relative movement between adjacent strands 36.

As the heart expands and contracts during diastole and systole, the contractile cells of the myocardium expand and contract. In a diseased heart, the myocardium may expand such that the cells are distressed and lose at least some contractility. Distressed cells are less able to deal with the stresses of expansion and contraction. As such, the effectiveness of heart pumping decreases.

As discussed above, and as discussed in more detail in the applications that are incorporated herein by reference, the undulating spring elements 34 exert a force in resistance to expansion of the heart 30. Collectively, the force exerted by the spring elements tends toward compressing the heart, thus alleviating wall stresses in the heart as the heart expands. Each strand of spring hinges is configured so that as the heart expands during diastole the spring hinges correspondingly expand, storing expansion forces as bending energy in the spring. As such, the stress load on the myocardium is partially relieved by the harness. This reduction in stress helps to decrease the workload of the heart, enabling the heart to more effectively pump blood and helping the myocardium cells to remain healthy and/or regain health.

It is to be understood that several embodiments of cardiac harnesses can be constructed and that such embodiments may have varying configurations, sizes, flexibilities, etc., yet still create a mildly compressive force on the heart so as to reduce wall stresses. As discussed in the above-referenced applications, such cardiac harnesses can be constructed from many suitable materials including various metals, fabrics, plastics and braided, woven and/or knit filaments. Suitable materials also include superelastic materials and materials that exhibit shape memory. For example, a preferred embodiment of a harness is constructed of Nitinol. Shape memory polymers can also be employed. Such shape memory polymers can include shape memory polyurethanes or other polymers such as those containing oligo(ecaprolactone) dimethacrylate and/or poly(e-caprolactone), which are available from mnemoScience. Further, some cardiac harness embodiments substantially encircle the heart, while others may employ spring members disposed over only a portion of the circumference of the heart or harness.

As just discussed, bending stresses are absorbed by the spring members 34 during diastole and are stored in the members as bending energy. During systole, when the heart pumps, the heart muscles contract and the heart becomes smaller. Simultaneously, bending energy stored within the spring members 34 is at least partially released, thereby providing an assist to the heart during systole. In a preferred embodiment, the compressive force exerted on the heart by the spring members of the harness comprises about ten percent to fifteen percent of the mechanical work done as the heart contracts during systole. Although the harness is not intended to replace ventricular pumping, the harness substantially assists the heart during systole.

Figure 5:
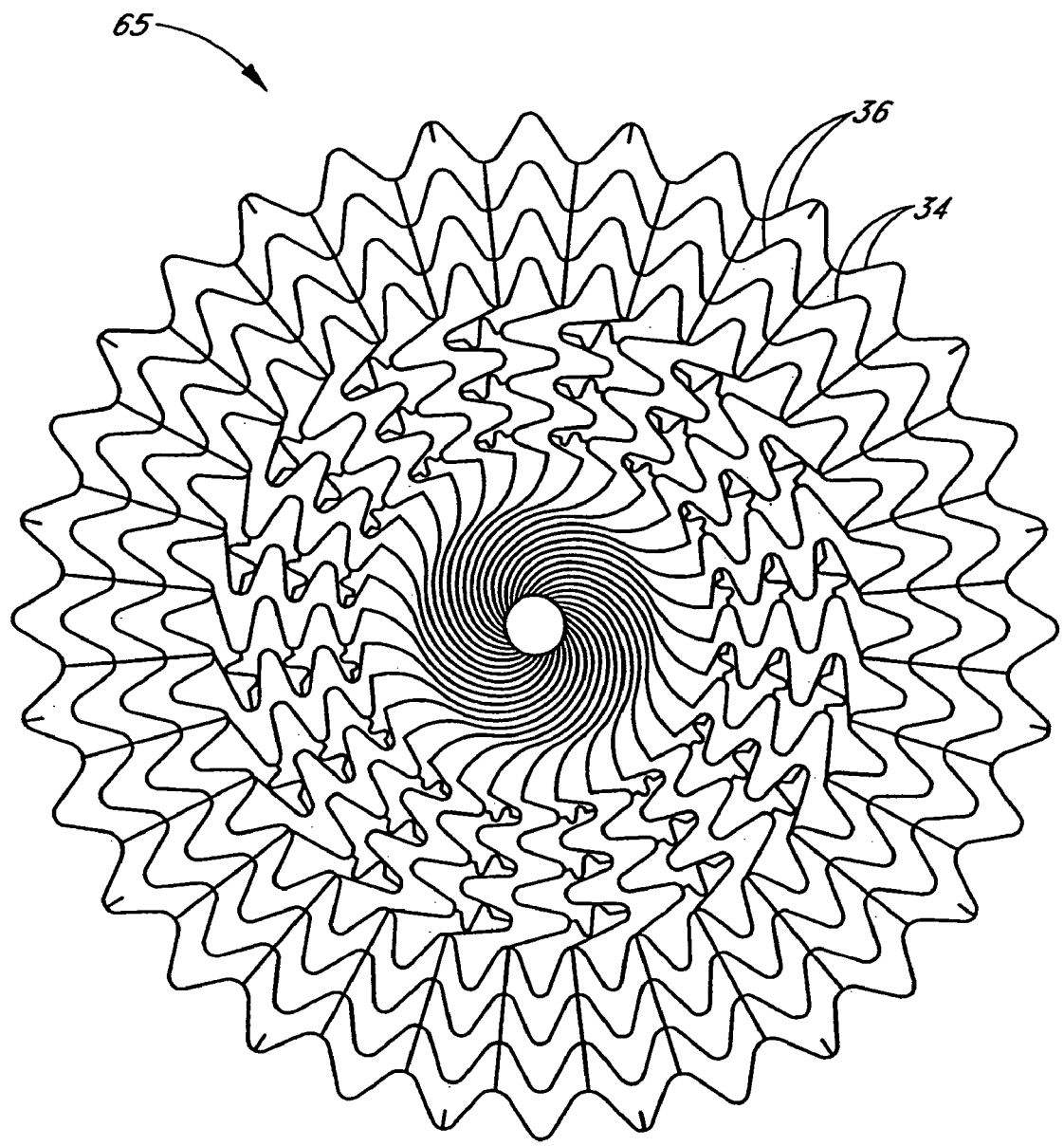
FIG. 5 shows another embodiment of a cardiac harness that has been cut out of a flat sheet of material.
Figure 6:
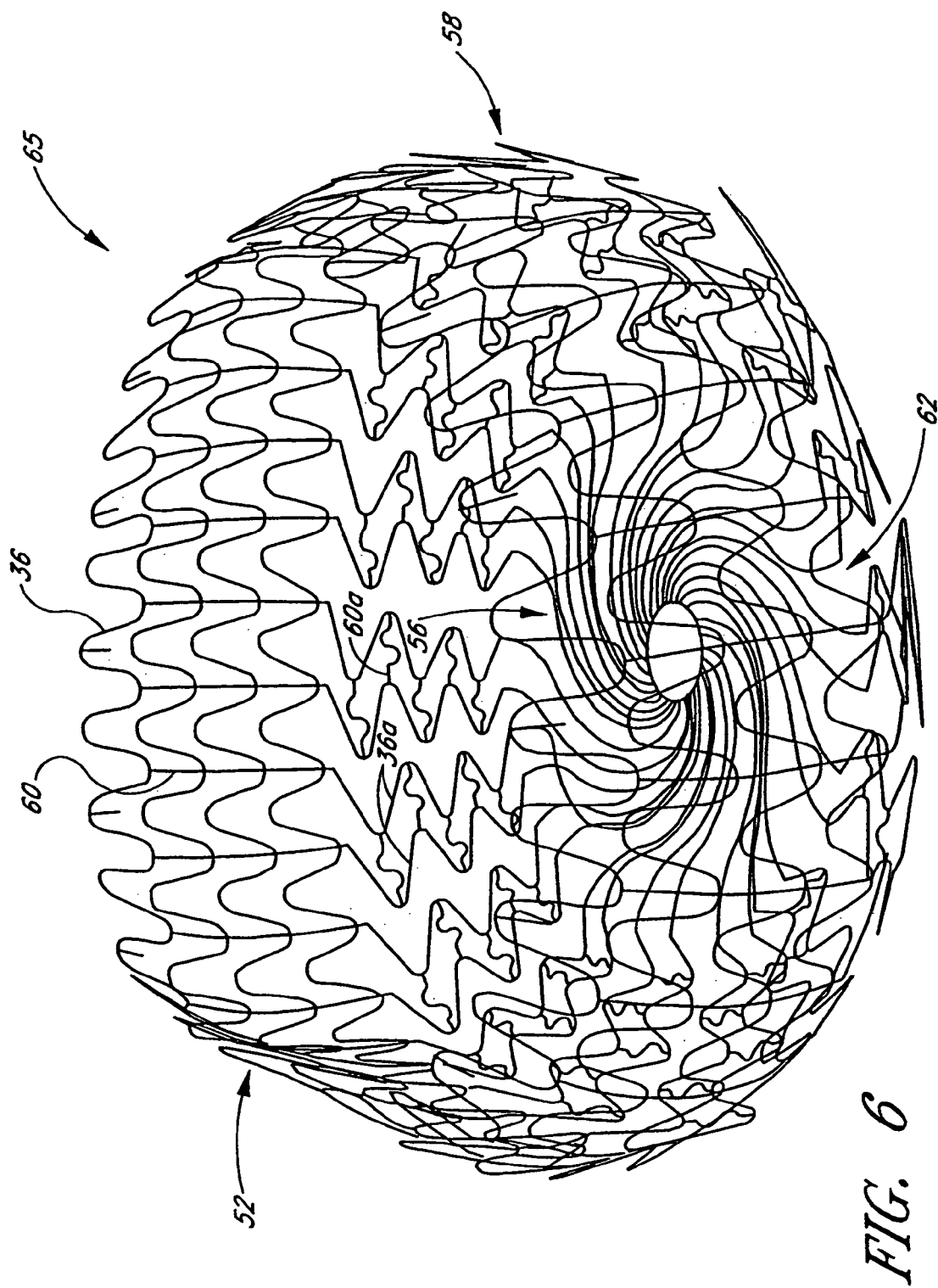
FIG. 6 shows the cardiac harness of FIG. 5 formed into a shape configured to fit about a heart.

With reference next to FIGS. 5 and 6, another embodiment of a harness 50 comprises strands 36 or strips of undulating wire. As discussed above, the undulations comprise hinges/spring elements 34 which are elastically bendable in a desired direction. The strands of spring elements are oriented in different directions and configured differently in the various portions of the harness. For example, as shown in FIGS. 5 and 6, in the base portion 52 of the harness, the strands are oriented so that the spring elements 34 will expand and contract in a direction generally transverse to a longitudinal axis of the heart. In the apex region 56, an "archimedes spiral" 62 configuration allows expansion and deformation in more than one direction, but is most compliant in a longitudinal direction. In the medial portion 58, strands 36a are oriented to expand and contract in a generally longitudinal direction. Additionally, some of the strands are connected to each other by interconnecting spring elements 60a, which allow the adjacent strands to move relative to each other in a transverse direction. However, some of the strands 36a in the medial portion 58 are not connected to others of the strands and can move freely relative to one another in a transverse direction. Thus, in the medial portion, the strands are collectively expandable in directions between the longitudinal and transverse directions.

In a mammalian heart, the heart muscle cells in the base region tend to expand and contract in a generally transverse direction during pumping of the heart. In the apex region, the heart muscles tend to expand and contract in a longitudinal direction. Between the apex and base regions of the heart, the heart muscles generally expand and contract in directions between the longitudinal and transverse directions. In the embodiment illustrated in FIGS. 5 and 6, the spring elements 34 are oriented generally in the directions of the cardiac muscle expansion so as to even better resist expansion and alleviate muscle stresses. As such, the arrangement of the base, medial and apex regions 52,58,56 of the harness is specially adapted to accommodate the natural expansion and contraction of heart muscle tissue. In this manner, the harness generally mimics the directional contractions typical of heart muscle.

Figure 7:
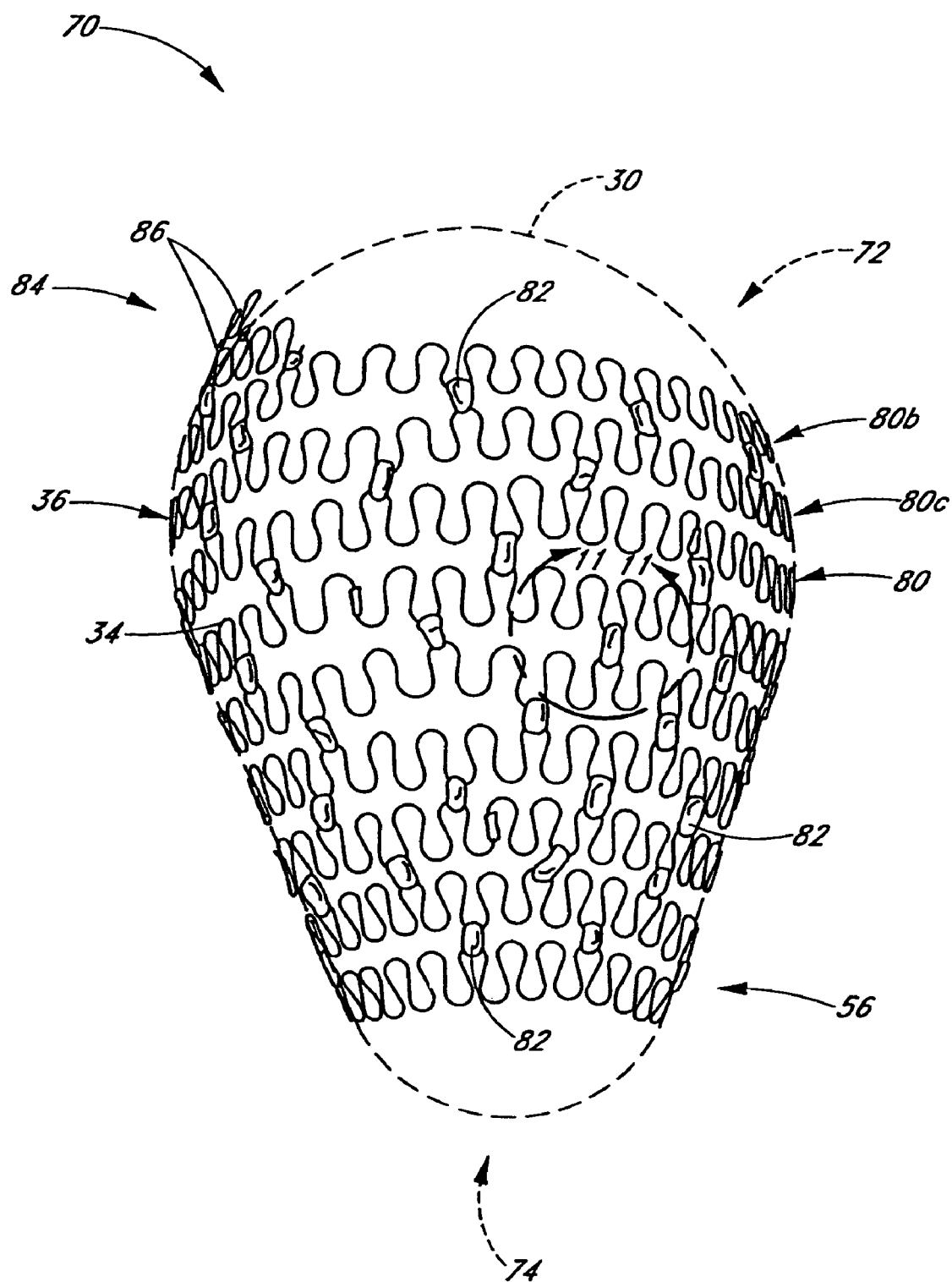
FIG. 7 is a schematic view of yet another embodiment of a cardiac harness, shown disposed upon a schematically-illustrated heart.

With next reference to FIG. 7, another embodiment of a cardiac harness 70 is illustrated disposed on a schematically illustrated heart 30. As shown, the cardiac harness 70 is configured to circumferentially surround the heart and extend longitudinally from a base portion 72 to an apex portion 74 of the heart. The harness 70 comprises a plurality of circumferentially extending rings 80 disposed longitudinally adjacent to one another. Each ring 80 comprises a plurality of interconnected spring members 34. The spring members 34 shown in FIG. 7 are substantially similar to the spring members 34 discussed above with reference to FIGS. 2A and 2B.

A plurality of connectors 82 interconnects adjacent rings 80. The connectors 82 have a length oriented longitudinally relative to the rings so as to create space between adjacent rings. Further, the connectors help to maintain proper alignment between adjacent rings, while allowing some relative movement therebetween. The illustrated harness is configured so that no spring members 34 overlap one another. As such, wear of the harness due to repeated flexing and relative movement of the spring members 34 is avoided. Preferably, the connectors 82 are formed of a semi-compliant material, such as silicone or other similar material. It is contemplated that the connectors 82 may comprise any medical grade polymer such as, but not limited to, polyethylene, polypropylene, polyurethane, nylon, PTFE and ePTFE.

In the embodiment illustrated in FIG. 7, each ring 80 initially comprises an elongate strand comprised of a series of spring members 34. Each strand of spring members 34 preferably is formed of a drawn metallic wire, preferably Nitinol or another metal having a shape memory property. Preferably, the Nitinol wire is shaped into the series of spring members and treated to develop a shape memory of the desired spring member structure. After such treatment, each elongate strand is cut to a length such that when opposite ends of the elongate strand are connected, the elongate strand assumes the ring-shaped configuration shown in FIG. 7.

It will be appreciated that the lengths of the elongate strands 36 are selected such that the resulting rings 80 are sized in conformity with the general anatomy of the patient's heart 30. More specifically, strands used in the apex portion of the harness are not as long as the strands used to form the base portion. As such, the harness generally tapers from the base 52 toward the apex 54 in order to generally follow the shape of the patient's heart. In another embodiment, the diameter of a ring 80b at the base of the harness is smaller than the diameter of the adjacent ring 80c. In this embodiment, the harness has a greatest diameter at a point between the base and apex ends, and tapers from that point to both the base and apex ends. Preferably, the point of greatest diameter is closer to the base end 52 than to the apex end 56. It is contemplated that the lengths of the strands, as well as the sizes of the spring members, may be selected according to the intended size of the cardiac harness 70 and/or the amount of compressive force the harness is intended to impart to the patient's heart.

With continued reference to FIG. 7, the right side 84 of the base portion 52 of the harness 70 comprises strands 86 of interconnected spring members that are not configured into a ring, but extend only partially about the circumference of the harness 80. Preferably, the partial strands 86 are connected to the adjacent full ring in a manner so that the partial strands are stretched. As such, the partial strands 86 will bend inwardly to "cup" the upper portion of the right atrium, as simulated in FIG. 7.

In the illustrated embodiment, the rings 80 are coated with dielectric material and the connectors 82 are formed of a nonconductive material. As such, each ring is electrically isolated from the other rings in the harness. Preferably, silicone tubing is advanced over a strand of spring members prior to forming the strand into a ring. In another embodiment, Nitinol wire is dip coated with an insulating material before or after being formed into rings.

Various materials and methods can be used to coat the harness with dielectric material. In the illustrated embodiment, the rings are coated with silicone rubber. Other acceptable materials include urethanes and ceramics, as well as various polymers and the like, including Parylene™, a dielectric polymer available from Union Carbide. The materials can be applied to a harness by various methods, such as dip coating and spraying, or any other suitable method.

As discussed above, adjacent rings 80 are joined to one another by connectors 82. In the embodiment illustrated in FIG. 7, connectors 82 are generally staggered between adjacent rings 80. It is to be understood that, in other embodiments, different arrangements of connectors 82 can be employed. For example, connectors between adjacent rings can be substantially aligned with one another.

In the embodiment illustrated in FIG. 7, the connectors 82 comprise silicone rubber. As such, the connectors are somewhat elastic, and the harness 70 is longitudinally compliant. However, the longitudinal compliance of the harness is limited by the elastic properties of the connectors. Due to both the geometry of the rings and elastic properties of the ring material, the circumferential compliance of the harness 70 is much greater than the longitudinal compliance. In an embodiment wherein connectors between adjacent rings are substantially aligned, the longitudinal compliance of the harness is even more closely limited by the elastic properties of the connectors, and such an embodiment would be less longitudinally compliant than the embodiment of FIG. 7.

When foreign objects or substances, such as a cardiac harness, are introduced onto or adjacent the heart, the body will tend to deposit tissue on or around the foreign object. For example, fibrin and collagen deposits will tend to accumulate on and around the heart after a cardiac harness is placed thereon. This scar tissue tends to be tough, though flexible, and will additionally resist expansion of the patient's heart.

In one preferred embodiment, a cardiac wall tension reduction device is constructed of a bioabsorbable material. As such, the device will dissolve after a predetermined period of time. When in place, however, the device will relieve cardiac wall tension. Once the device is installed on the heart, the patient's body will respond by depositing scar tissue on the device and around the heart. Preferably, the tissue at least partially encapsulates the heart. After the device dissolves, the scar tissue remains. Thus, although the implanted device no longer restricts or resists further cardiac expansion, the scar tissue resists such expansion. As such, a long term treatment for resisting further cardiac expansion is established without requiring a permanent implant.

A bioabsorbable cardiac wall tension reduction device can be formed of any bioabsorbable material. It is to be understood that many types of materials can be used, including bioabsorbable materials typically used in sutures, stents and the like. For purposes of this disclosure, bioabsorbable materials include materials that degrade or dissolve over time when placed within a human body, and include biodegradable materials. In preferred embodiments, FDA-approved materials such as polylactic acid (PLA) and polyglycolic acid (PGA) can be used. Other materials, including both synthetic and naturally-derived polymers can suitably be employed.

A bioabsorbable cardiac harness can be formed in accordance with any acceptable method and fashion. For example, a sheet of PGA or PLA can be molded to a shape that fits about the heart. Similarly, a sheet can be formed having holes or gaps that lend themselves to increased flexibility. Further, a device can be molded or cut to have a series of undulating spring members, as in the embodiments discussed above. Still further, a lattice structure may be used to provide elasticity and facilitate and/or direct scar growth in a desired manner and direction. Still further, bioabsorbable material can be provided as extruded fibers or filaments that can be woven, braided, knit, or the like so as to fit about the heart and constrain expansion thereof.

As discussed in the above-referenced applications, when a force is applied to relieve cardiac wall stresses, the working load on the heart is reduced. Reducing the working load allows the heart to at least partially rest, and appears to provide an opportunity for the heart to at least partially heal itself. For example, it is anticipated that a remodeled diseased heart can reverse-remodel so as to become more healthy if cardiac wall stresses are reduced. The effect of reducing wall stress can indeed lead to valuable and beneficial healing effects.

In another preferred embodiment, a cardiac wall tension reduction device is at least partially made of a bioabsorbable material that is combined with medically beneficial medicaments so that the beneficial medicaments are released as the bioabsorbable material dissolves. For example, bone marrow or stem cells can be provided so as to possibly stimulate myocardial regeneration. This type of treatment may help resolve an infarct, and promote healing of the heart. Of course, it is to be understood that any type of medicament anticipated to aid the heart can be combined with a bioabsorbable apparatus.

In another embodiment, a bioabsorbable cardiac harness can be combined with anti-fibrin drugs and/or other medications that resist the deposit or growth of body tissues around the installed harness. As such, the harness reduces heart wall stresses, giving the heart an opportunity to begin healing, but will not form extensive scar tissue. In this embodiment, the harness is adapted so that it will dissolve after a period of time sufficient to rest the heart so that it can continue its work without developing worsening symptoms of disease. Since little or no scar tissue is left behind after the harness dissolves, the rested heart will not be restricted by such tissue. Although, as discussed above, scar tissue can sometimes serve a beneficial purpose, some situations benefit from avoidance of scar tissue.

As discussed above, it is anticipated that the heart will reverse remodel when a harness reduces cardiac wall stress. As such, the heart may be smaller when a bioabsorbable harness dissolves than when the harness was installed. In accordance with one embodiment, a new, smaller harness is then to be placed on the heart, thus prompting further reverse remodeling. This process can be repeated as often as desired, until the heart has reached a desired size and health level. When the desired size is achieved, further harnesses may not be needed because the heart is healthy enough to maintain its size. Alternatively, a permanent harness may be installed to maintain the heart at the desired size. In a further embodiment, another bioabsorbable harness is installed, but without anti-tissue-growth drugs. As such, the heart becomes at least partially encapsulated in body tissues that will resist enlargement of the heart beyond the desired size. This helps the heart maintain the desired healthy size.

In still another preferred embodiment, foreign bodies are introduced about the heart so as to stimulate tissue growth that will at least partially encapsulate the heart. These foreign bodies need not be in the form of a cardiac harness, and need not impart any compressive force on the heart. However, these foreign bodies will stimulate fibrin/collagen or other tissue growth about the heart so as to at least partially encapsulate the heart in the tissue. The tissue will act as a sock or jacket to resist further expansion of the heart.

It is to be understood that such foreign matter can be bioabsorbable, but is not necessarily so. For example, the foreign matter can comprise a liquid or powder irritant specially adapted to stimulate fibrin or collagen growth. Such irritants may include shredded or powderized polyester or other plastics.

Figure 8:
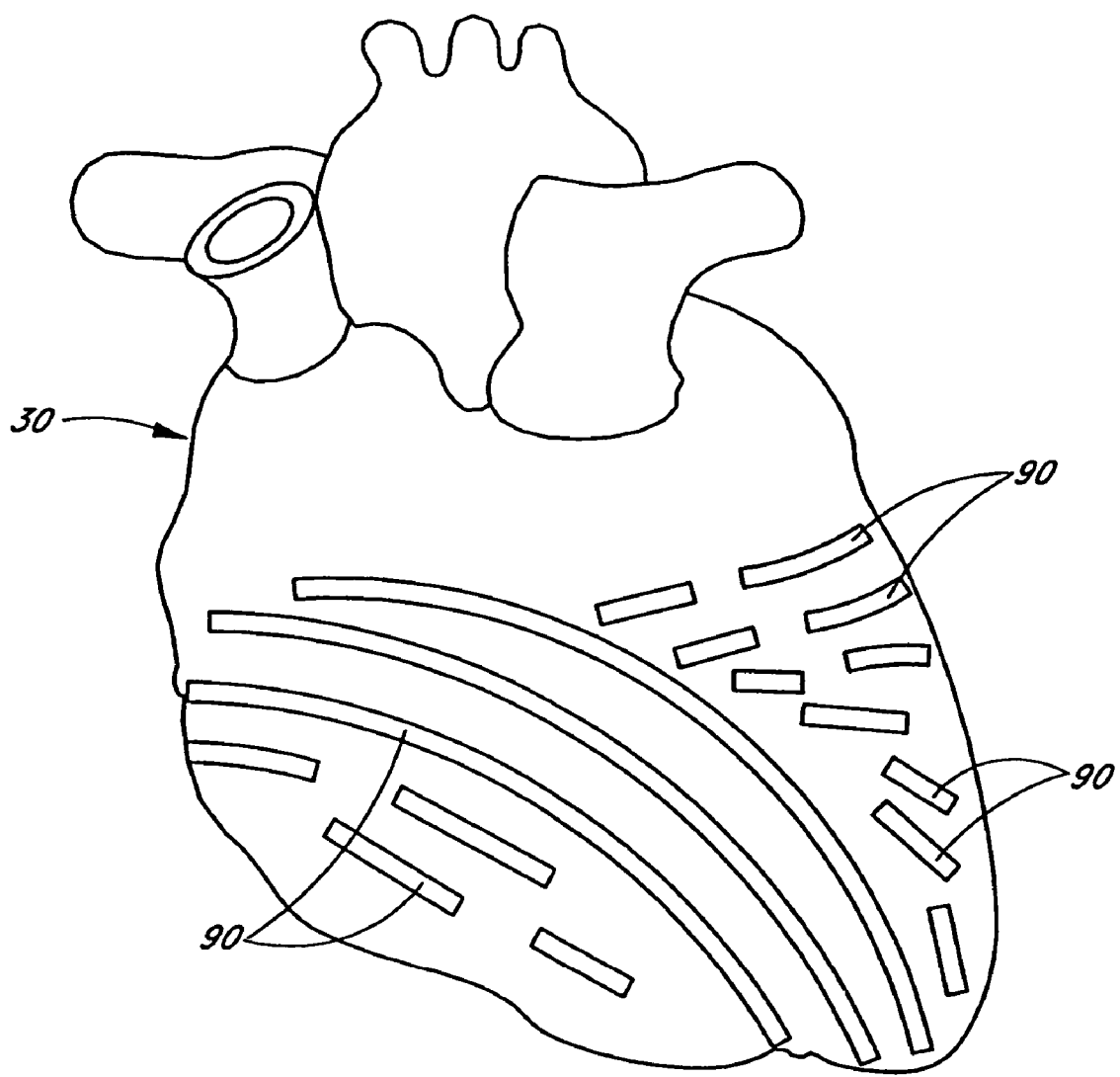
FIG. 8 illustrates a plurality of strips of material arranged on a patient's heart.

In another embodiment, foreign matter or a cardiac harness can be arranged around the heart so as to stimulate tissue growth at specified locations and in desired directions. For example, matter can be placed so as to stimulate tissue growth in a configuration that generally follows the directional expansion and contraction of heart muscle. For example, in FIG. 8, foreign material is arranged on or around the heart 30 in a series of strips 90 which are arranged to generally correspond to the directional expansion and contraction of heart muscle. This prompts tissue growth in the area and directional configuration of the strips 90. As such, the tissue grows to generally correspond to the directional expansion and contraction of heart muscle. Such tissue will help reduce the muscle load as the heart expands during filling and contracts during pumping. Preferably, the foreign matter that stimulates the tissue growth comprises a bioabsorbable material. In another embodiment, the foreign matter is not bioabsorbable and is maintained permanently in the patient's body.

Introduction and placement of foreign material around the patient's heart can be performed via minimally-invasive methods. Minimally invasive methods can also be used to install a Nitinol, woven and/or bioabsorbable harness around the heart. Even less invasive methods can be used to place loose or detached foreign matter about the heart.

As a patient's heart enlarges during congestive heart failure, the annulus of certain valves, such as the mitral valve, tends to grow with the heart. Eventually, the valve annulus may increase in size to a point at which the leaflets are not large enough to completely close the valve. Another factor contributing to valve dysfunction is that as the heart enlarges, the geometry of the heart changes somewhat. Portions of the heart, such as the papillary muscles, are moved outwardly from the leaflets to which the papillary muscles are attached via the chordae tendinaea. These papillary muscles may be stretched so much that they prevent the valve leaflets from adequately engaging each other during valve closure. As such, the leaflets will not be able to fully close, and the valve will leak. Such valve leakage simply makes the patient's heart problems worse.

Figure 9:
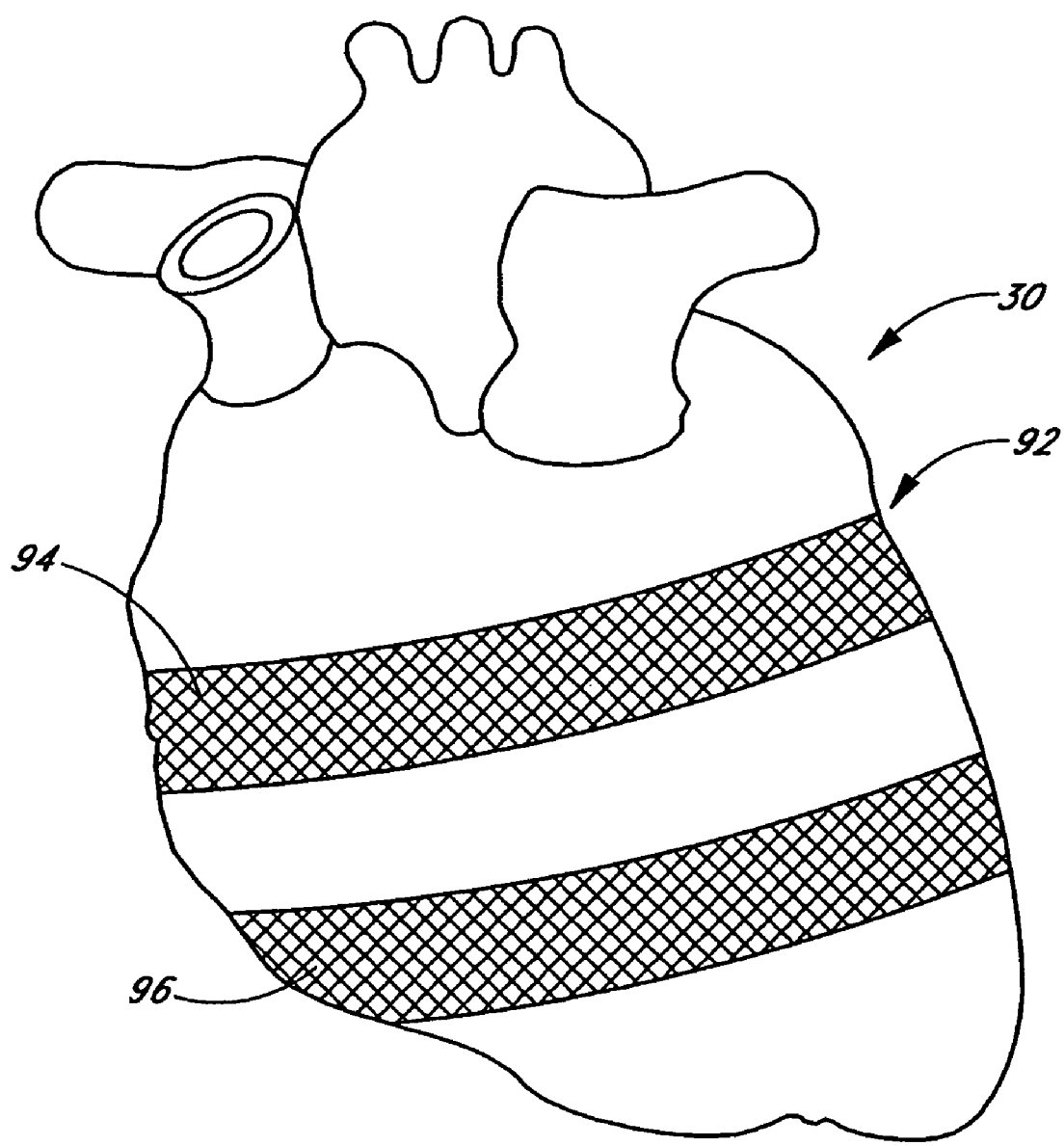
FIG. 9 illustrates embodiments of an AV groove collar and a papillary muscle band disposed on a patient's heart.

As discussed in the above-referenced application entitled "Heart Failure Treatment Device and Method," a harness or collar can be configured to exert a compressive force on specific portions of a heart so as to help prevent or diminish valve dysfunction. For example, a collar-type device can be specially configured to fit around the AV groove region 92 of the heart 30. FIG. 9 shows an AV groove collar 94 arranged and configured to exert a compressive force that will tend to decrease the size of the valvular annuli and/or prevent enlargement of the valvular annuli beyond desired sizes.

With continued reference to FIG. 9, a papillary muscle band 96 can be configured to be placed around the outside of the heart 30 in the area of the papillary muscles. As known in the art, the papillary muscles are generally midway between the AV groove and the apex of the heart. Thus, a papillary muscle band 96 can exert a compressive force to reduce the diameter of the heart at the level of the papillary muscles. This will help the papillary muscles become less stretched so that they allow and facilitate closure of the valve leaflets. In the illustrated embodiment, the papillary band 96 is constructed of a woven or knit fabric. It is to be understood that the papillary band 96 can also have an undulating spring hinge construction such as that shown and discussed in connection with the embodiments presented in FIGS. 1-7. Further, the AV groove collar 94 and/or papillary muscle band 96 can be constructed of a substantially elastic material, such as silicone rubber.

As discussed above, a cardiac harness applies a mild compressive force on a patient's heart. It is anticipated that embodiments of an AV groove collar 94 and papillary muscle band 96 will exert a more aggressive compressive force than a typical cardiac harness. In another embodiment, a permanent cardiac harness implant is coated with an irritant in the portions configured to engage the AV groove 92 and/or papillary muscle regions of the heart so as to provide a more dramatic stimulus for tissue growth in these portions. Thus, tissue growth in the AV groove and papillary muscle areas of the heart will be increased, providing further resistance to expansion in these areas.

In another embodiment, a bioabsorbable woven or knit AV groove collar 94 stimulates tissue growth in and around the AV groove so as to provide similar benefits without a permanent implant. A bioabsorbable papillary muscle band 96 is similarly provided. It is to be understood that the AV groove collar 94 and papillary muscle band 96 can be used independent of one another or in conjunction with one another and either independent of or in conjunction with a permanent or bioabsorbable cardiac harness. For example, a papillary muscle band can be placed on the heart before or after installation of a cardiac harness.

In still further embodiments, an AV groove collar 94 and papillary band 96 can be incorporated into a cardiac harness so as to apply specially-directed forces to the specific portions of the heart and to create specific regions of increased tissue growth.

In still another embodiment, an AV groove collar and/or papillary band is constructed of a bioabsorbable material and is configured to exert a force on a patient's heart within a first force range. A cardiac harness is provided and is configured to exert a force on the patient's heart within a second force range. The first range of force, which is to be exerted by the papillary band or AV groove collar, induces generally greater levels of force than the second range. As such, when the combination is installed on the patient's heart, a greater force is exerted at the AV groove or papillary band region of the heart than elsewhere. As time passes and the collar or band is absorbed, the applied force on the heart becomes more equalized. This arrangement enables treatment of acute valvular dysfunction by applying a greater degree of force in one area of the heart than is needed for the rest of the heart. Over time, as the rest of the heart remodels, no extra force is needed to treat valvular dysfunction and, in this embodiment, is no longer exerted.

In a variation of the above embodiment, the AV groove collar and/or papillary muscle band is formed from a bioabsorbable material and is configured to have a maximum dimension beyond which the collar/band will not deform. As such, a selected portion of the heart can be constrained to a specific size while the rest of the heart is not so constrained. This enables passive treatment of the heart as a whole while also addressing an acute issue. It is to be understood that, in other embodiments, a bioabsorbable member can temporarily apply a targeted, increased force in a desired portion of the patient's heart while an accompanying cardiac harness provides a more even, mild and permanent compressive force over a larger portion of the heart.

In the embodiments described above, the cardiac harness preferably applies a mild compressive force on the heart in order to achieve therapeutic benefits. An applied force or pressure within a therapeutic range is defined herein as a pressure of sufficient magnitude that, when applied to an organ such as the heart, results in a benefit to the organ. In one embodiment, the therapeutic range for a cardiac harness is between about 2-20 mmHg. More preferably, the therapeutic pressure is about 2-10 mmHg, and most preferably is between about 2-5 mmHg.

Figure 10:
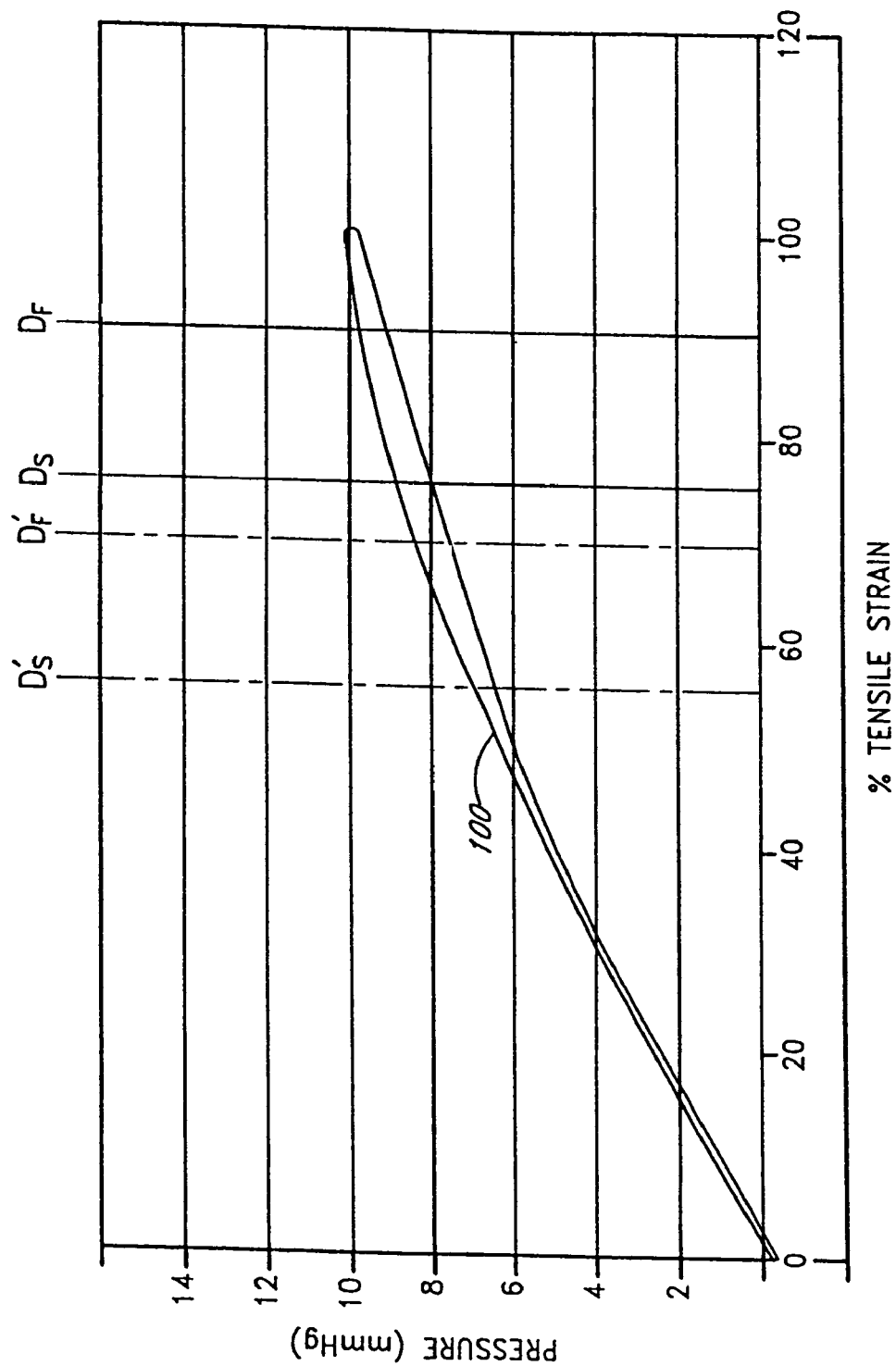
FIG. 10 shows a curve representing test data for one embodiment of a cardiac harness.

With reference next to FIG. 10, a pressure versus percentage tensile strain curve 100 is presented reflecting actual test data for one embodiment of a cardiac harness constructed of drawn Nitinol wire formed into undulating spring hinges. As shown, this harness embodiment is capable of extensive deformation. In this embodiment, the harness is stretched from its original, at-rest position in order to be fit over the patient's heart. When on the heart, it applies a mild, compressive force, which will tend to help the heart reverse-remodel. As the heart reverse-remodels and becomes smaller, the harness correspondingly becomes smaller. Of course, the size of the heart varies between the beginning of diastole and the end of diastole. In the illustrated embodiment, the labels $D_S$ and $D_F$ have been applied to the curve to identify the pressure applied by the harness at a particular level of tensile strain and corresponding to the beginning $D_S$ and end $D_F$ of diastole. In a similar manner the labels $D'_S$ and $D'_F$ illustrate the relative pressures applied by the harness at the beginning and end of diastole as the heart reverse remodels and becomes smaller. In the illustrated embodiment, the cardiac harness adjusts continuously with the heart as the heart changes in size, and also applies a therapeutic pressure to the heart even when the heart reverse remodels extensively.

In the illustrated embodiment, the cardiac harness exerts a pressure in response to strain of the harness. For example, if the harness is strained about one hundred percent it will exert about 10 mm Hg on the heart. As the heart becomes smaller as a result of reverse remodeling, the percent strain of the harness will decrease, and the corresponding pressure exerted by the harness also will decrease. In the preferred embodiment, the harness is configured so that the applied pressure varies relatively little over a broad range of deformation. As such, the harness provides a therapeutic pressure even after the heart has reverse remodeled extensively.

For example, with continued reference to FIG. 10, a reduction in size corresponding to a forty percent change in strain as the harness reduces from one hundred percent strain to sixty percent strain is accompanied by a decrease in applied pressure of less than about 3 mm Hg. A forty percent change from eighty percent to forty percent strain is accompanied by a decrease in applied pressure of less than about 4 mm Hg. Still further, a twenty percent reduction in size can be accompanied by a decrease in applied pressure of less than about 3 mm Hg or, depending on the degree of strain of the harness, less than about 2 mm Hg. Additional relationships indicating changes in applied pressure corresponding to changes in the size/strain of the harness can be derived from the illustrated pressure/strain curve of FIG. 10.

In accordance with another embodiment, the harness represented by the test data of FIG. 10 is coated with a bioabsorbable coating including a medicament that inhibits growth of tissue in response to introduction of a foreign body. As such, scar tissue growth around the heart and harness will be minimized, and the harness can dramatically decrease in size as the heart reverse remodels without scar tissue preventing the harness from adjusting and changing shape with the patient's heart.

Figure 11:
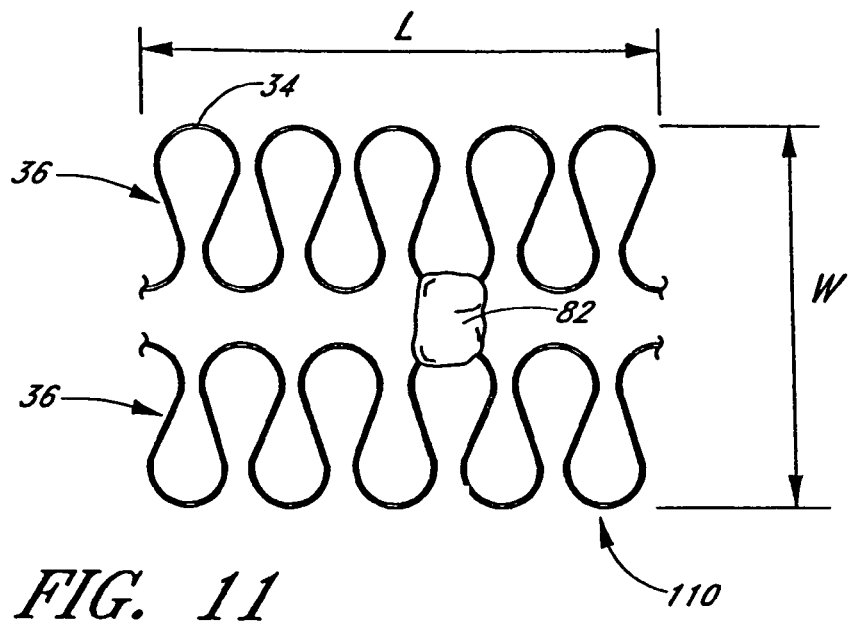
FIG. 11 shows a test portion which has been cut out of the cardiac harness of FIG. 7 generally along line 11-11.
Figure 12:
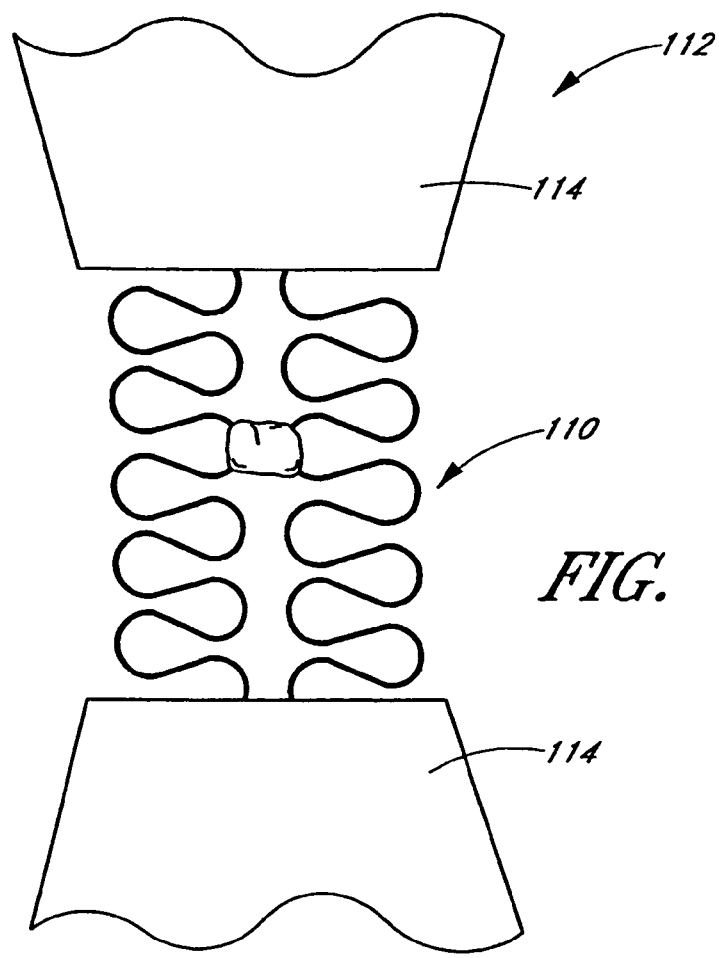
FIG. 12 shows the test portion of FIG. 11 in a material testing machine.
Figure 13:
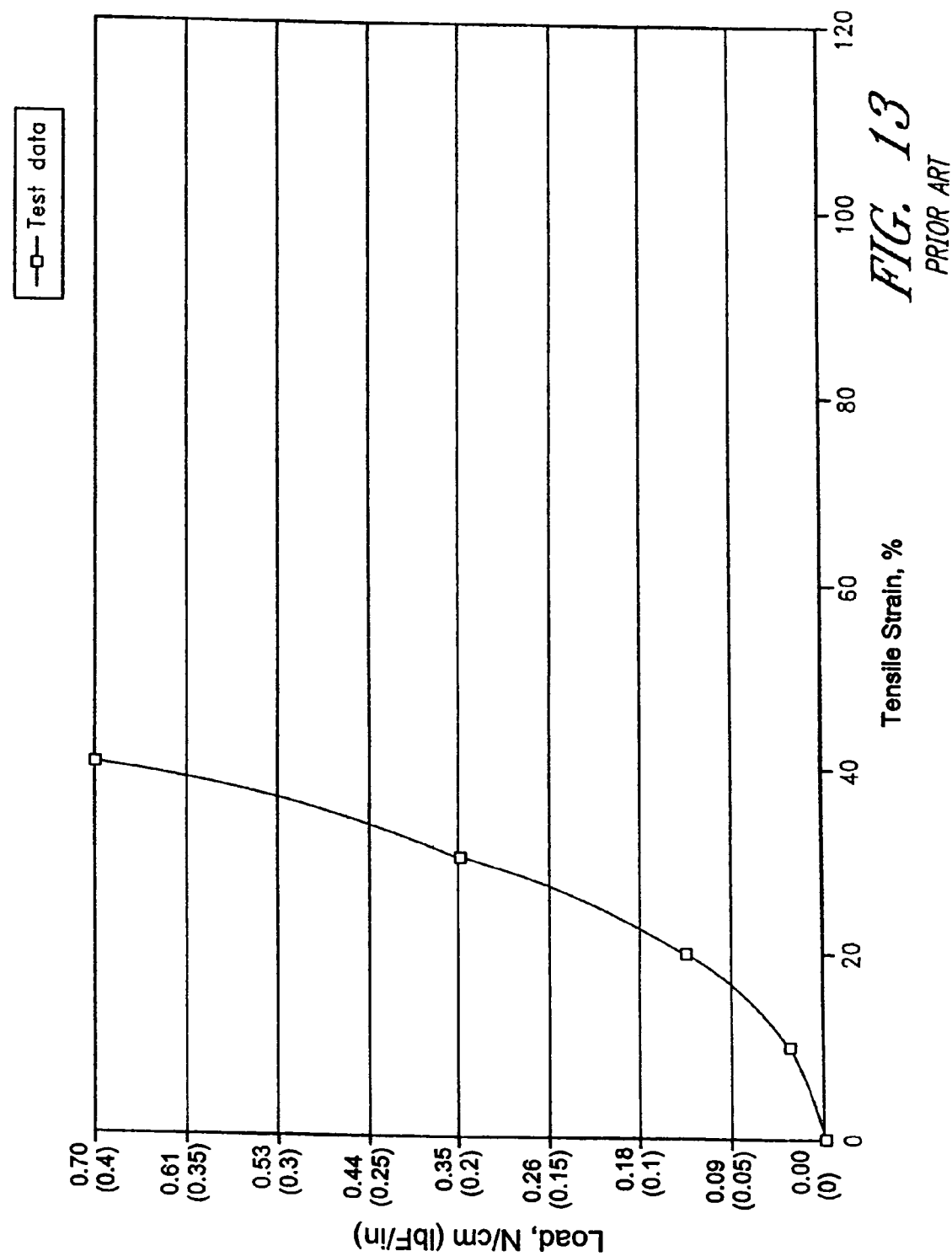
FIG. 13 shows a curve representing test data for a cardiac harness constructed of a knit material.

With reference next to FIGS. 11 and 12, applicants have developed a method and apparatus for testing the elastic behavior of a cardiac harness. FIG. 11 shows an elongate test portion 110 that is taken from a cardiac harness. In the illustrated embodiment, the test portion 110 has been taken from the harness 70 of FIG. 7 generally along the lines 11-11. However, it is to be understood that a test portion can be taken from nearly any portion of a harness so long as the test portion comprises a substantial enough portion of the harness so as to properly represent the harness during materials testing. With continued reference to FIG. 11, the test portion 110 preferably has a length L and a width W. The length L is defined in a direction generally along the circumference of the harness. In other words, the length L is taken in a direction generally transverse to a longitudinal axis of the heart and harness. Most preferably, the length L is taken in the direction generally perpendicular to the longitudinal axis. The width W extends in a direction generally along the longitudinal axis.

With reference next to FIG. 12, the test portion 110 preferably is placed in a material property testing machine 112 such as is available from Instron™. The test portion 110 of the harness preferably is disposed in mounts 114 of the materials testing machine 112, and the machine pulls the test portion 110 along its length L. The materials testing machine 112 collects data detailing the load, in pounds force (lbF), and the corresponding percent tensile strain of the test portion 110 along the length L. The load is then normalized with reference to the width W of the test portion which, in the illustrated embodiment, is in a longitudinal direction. Thus, in the illustrated embodiment, load data is taken in the units of lbF/in.

The above-described test procedure allows measurement of the elasticity/deformation behavior of various embodiments of cardiac harnesses so that such embodiments can be compared. For consistency, testing preferably is performed at room temperature, preferably about 37° C. (98.6° F.). As discussed above, the load is applied along the length L of the test portion 110, which length L is taken in a direction along the circumference of the corresponding harness. Thus, the applied load represents and corresponds to a circumferential load of the harness. The percent tensile strain is also taken along the length L. As such, the percent tensile strain represents and corresponds to a percent of circumferential expansion of the harness above a zero load condition.

Figure 14:
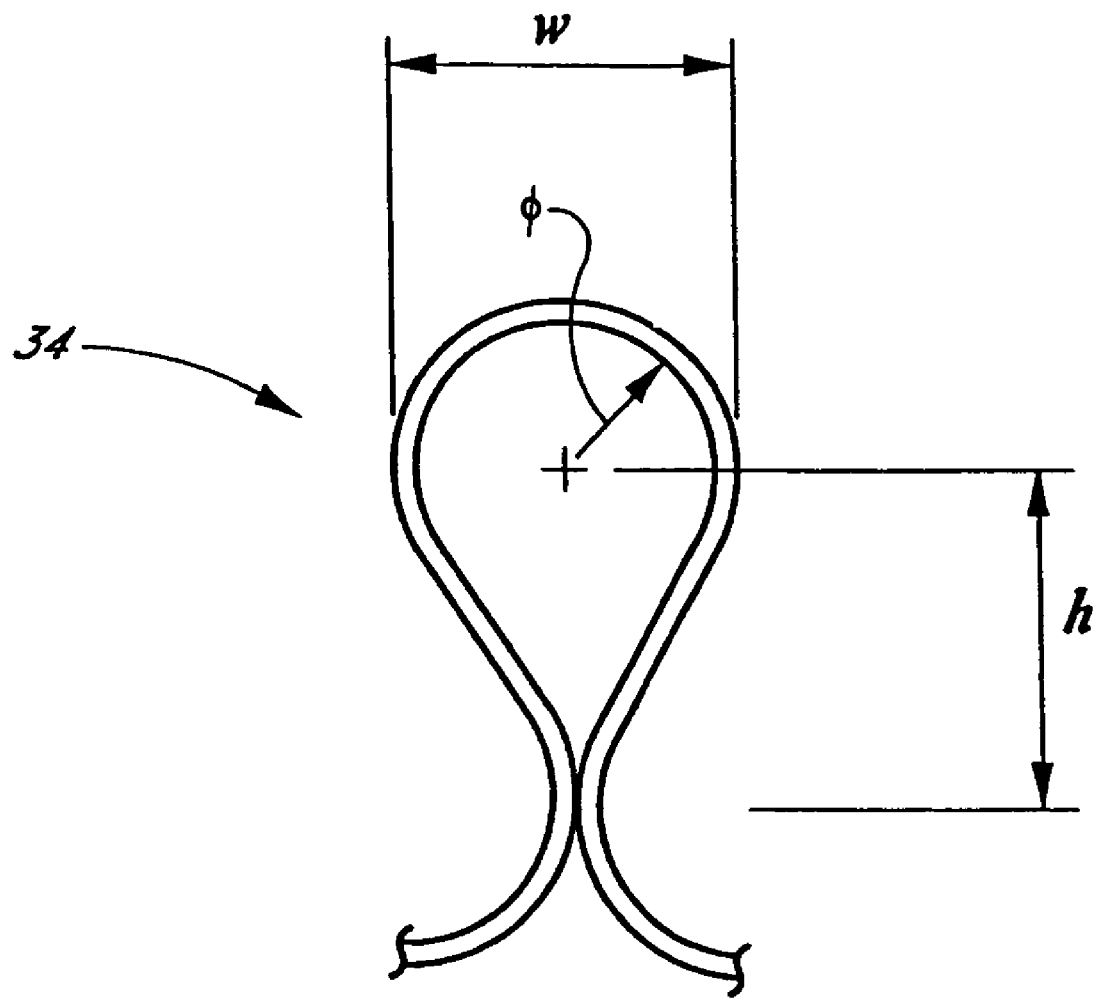
FIG. 14 shows a schematic view of one typical spring element of a test portion as in FIG. 11.

With reference next to FIG. 14, an exemplary spring element 34 of a harness such as the harness 70 of FIG. 7 is illustrated. The spring element 34 of FIG. 14 represents one element from a strand of such spring elements. This figure will be used to define the dimensions of some specific embodiments for which test data has been obtained.

Figure 15:
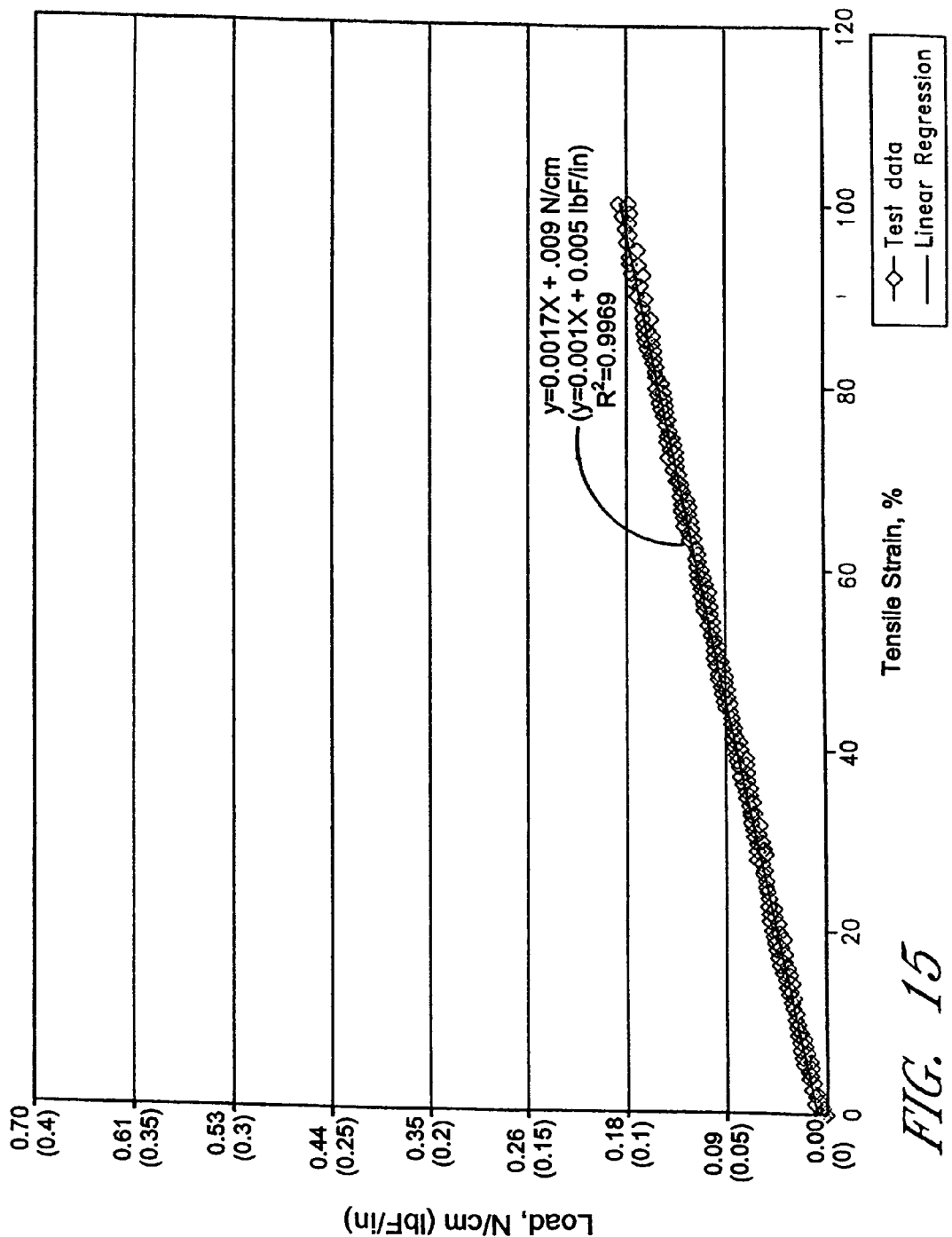
FIG. 15 shows test data and a linear regression line generated therefrom in accordance with one embodiment of a cardiac harness.

With reference also to FIG. 15, plotted test data is presented for a test portion of a cardiac harness. The cardiac harness exemplified by the test data of FIG. 15 comprises strands of spring elements preferably formed of drawn Nitinol wire having a diameter of about 0.020 cm (0.008 in). The spring elements resemble the spring element 34 shown in FIG. 14, and have a width w of about 0.419 cm (0.165 in), a height h of about 0.414 cm (0.163 in), and a diameter φ of about 0.320 cm (0.126 in). After the wire is formed into strands of spring elements, it is heat treated at about 485° C. (905° F.) for about thirty minutes. Silicone tubing having an inner diameter of about 0.025 cm (0.010 in) and an outer diameter of about 0.064 cm (0.025 in) is disposed over the strand.

A test portion of the just-described cardiac harness was tested in a materials testing machine in accordance with the procedure discussed above. Test data, including load and percent tensile strain, was collected between a zero load, zero percent strain condition and about a one hundred percent strain condition. Representative test data points are set out in the plot of FIG. 15, in which percent tensile strain is plotted along the x axis, and load, normalized with respect to the width W of the test portion, is plotted along the y axis.

With continued reference to FIG. 15, a linear regression of the test data was performed in order to derive a function describing the behavior of the cardiac harness in the form y=ax+b. The linear regression was performed using Microsoft™ Excel™ software, and yielded the function y=0.0017x+0.009 N/cm (y=0.001x+0.005 lbF/in). The linear regression function has a coefficient of determination $R^2$ of about 0.9969. It is understood that, in linear regression, the coefficient of determination $R^2$ represents how well the linear regression function represents the collection of data. In the illustrated embodiment the $R^2$ value is very close to 1, and thus indicates that the linear regression line closely represents the data.

Figure 16:
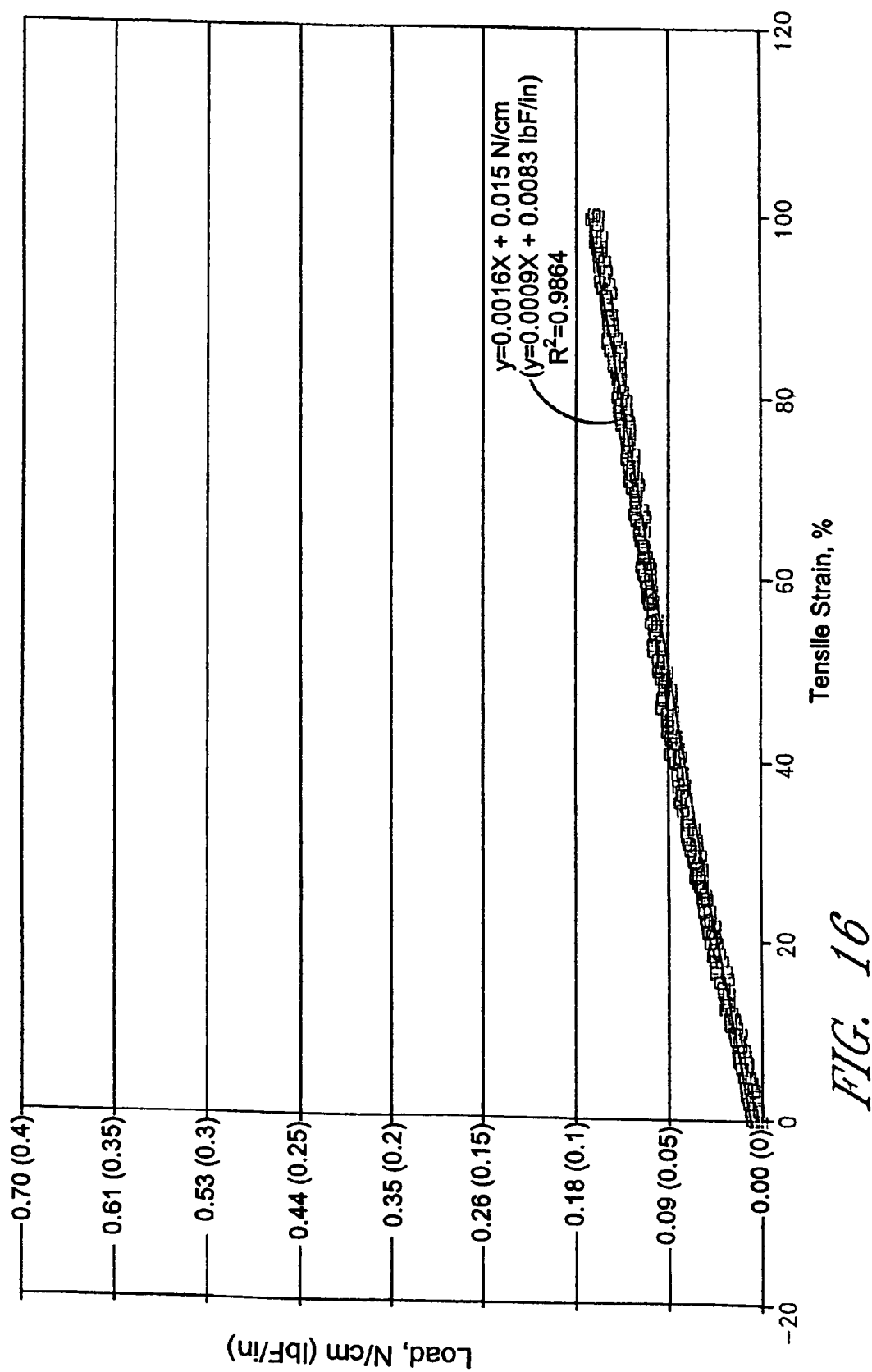
FIG. 16 shows test data and a linear regression line derived therefrom in connection with another embodiment of the cardiac harness.

With reference next to FIG. 16, plotted test data is presented for a test portion of another embodiment of a cardiac harness. The cardiac harness exemplified by the test data of FIG. 16 comprises strands of spring elements preferably formed of drawn Nitinol wire having a diameter of about 0.031 cm (0.012 in). The spring elements resemble the spring element 34 shown in FIG. 14, and have a width w of about 0.762 cm (0.300 in), a height h of about 0.699 cm (0.275 in), and a diameter φ of about 0.635 cm (0.250 in). After the wire is formed into strands of spring elements, it is heat treated at about 485° C. (905° F.) for about 30 minutes. Silicone tubing having an inner diameter of about 0.036 cm (0.014 in) and an outer diameter of about 0.074 cm (0.029 in) is disposed over the strand.

A test portion of the just-described cardiac harness was tested in a materials testing machine in accordance with the procedure discussed above. Test data, including load and percent tensile strain, was collected between a zero load, zero percent strain condition and about a one hundred percent strain condition. Representative test data points are set out in the plot of FIG. 16, in which percent strain is plotted along the x axis, and load, normalized with respect to the width W of the test portion, is plotted along the y axis.

With continued reference to FIG. 16, a linear regression of the test data was performed in order to derive a function describing the behavior of the cardiac harness in the form y=ax+b. The linear regression was performed using Microsoft™ Excel™ software, and yielded the function y=0.0016x+0.015 N/cm (y=0.0009x+0.0083 lbF/in.). The linear regression function has a coefficient of determination $R^2$ of about 0.9864.

Figure 17:
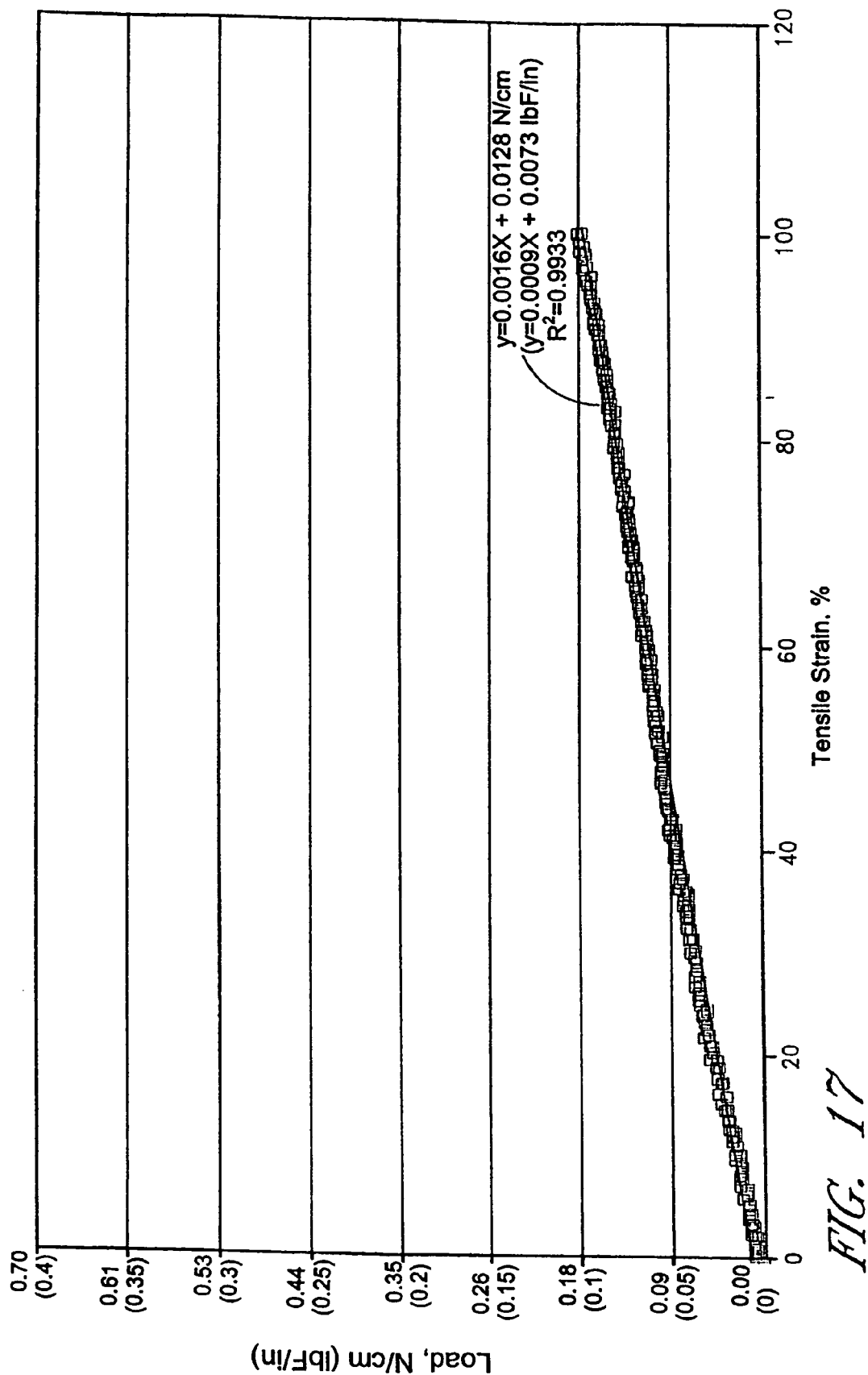
FIG. 17 shows test data and a linear regression line derived therefrom for yet another embodiment of the cardiac harness.

With reference next to FIG. 17, plotted test data is presented for a test portion of yet another embodiment of a cardiac harness. The cardiac harness exemplified by the test data of FIG. 17 comprises strands of spring elements preferably formed of drawn Nitinol wire having a diameter of about 0.031 cm (0.012 in.). The spring elements resemble the spring element 34 shown in FIG. 14, and have a width w of about 0.762 cm (0.300 in.), a height h of about 0.699 cm (0.275 in.), and a diameter φ of about 635 cm (0.250 in). After the wire is formed into strands of spring elements, it is heat treated at about 485° C. (905° F.) for about 30 minutes. Silicone tubing having an inner diameter of about 0.036 cm (0.014 in.) and an outer diameter of about 0.074 cm (0.029 in.) is disposed over the strand. As can be seen, the cardiac harness represented in FIG. 17 is structurally very similar to the cardiac harness represented in FIG. 16. In fact, the most significant difference between the harnesses is found in the arrangement of connectors between adjacent strands. As discussed above, due to the differences in connector placement, the longitudinal compliances of these embodiments are somewhat different. However, as set out below, the circumferential compliance of these embodiments is quite similar.

A test portion of the just-described cardiac harness was tested in a materials testing machine in accordance with the procedure discussed above. Test data, including load and percent tensile strain, was collected between a zero load, zero percent strain condition and about a one hundred percent strain condition. Representative test data points are set out in the plot of FIG. 17, in which percent strain is plotted along the x axis, and load, normalized with respect to the width W of the test portion, is plotted along the y axis.

With continued reference to FIG. 17, a linear regression of the test data was performed in order to derive a function describing the behavior of the cardiac harness in the form y=ax+b. The linear regression was performed using Microsoft™ Excel™ software, and yielded the function y=0.0016x+0.0128 N/cm (y=0.0009x+0.0073 lbF/in.). The linear regression function has a coefficient of determination $R^2$ of about 0.9933.

Figure 18:
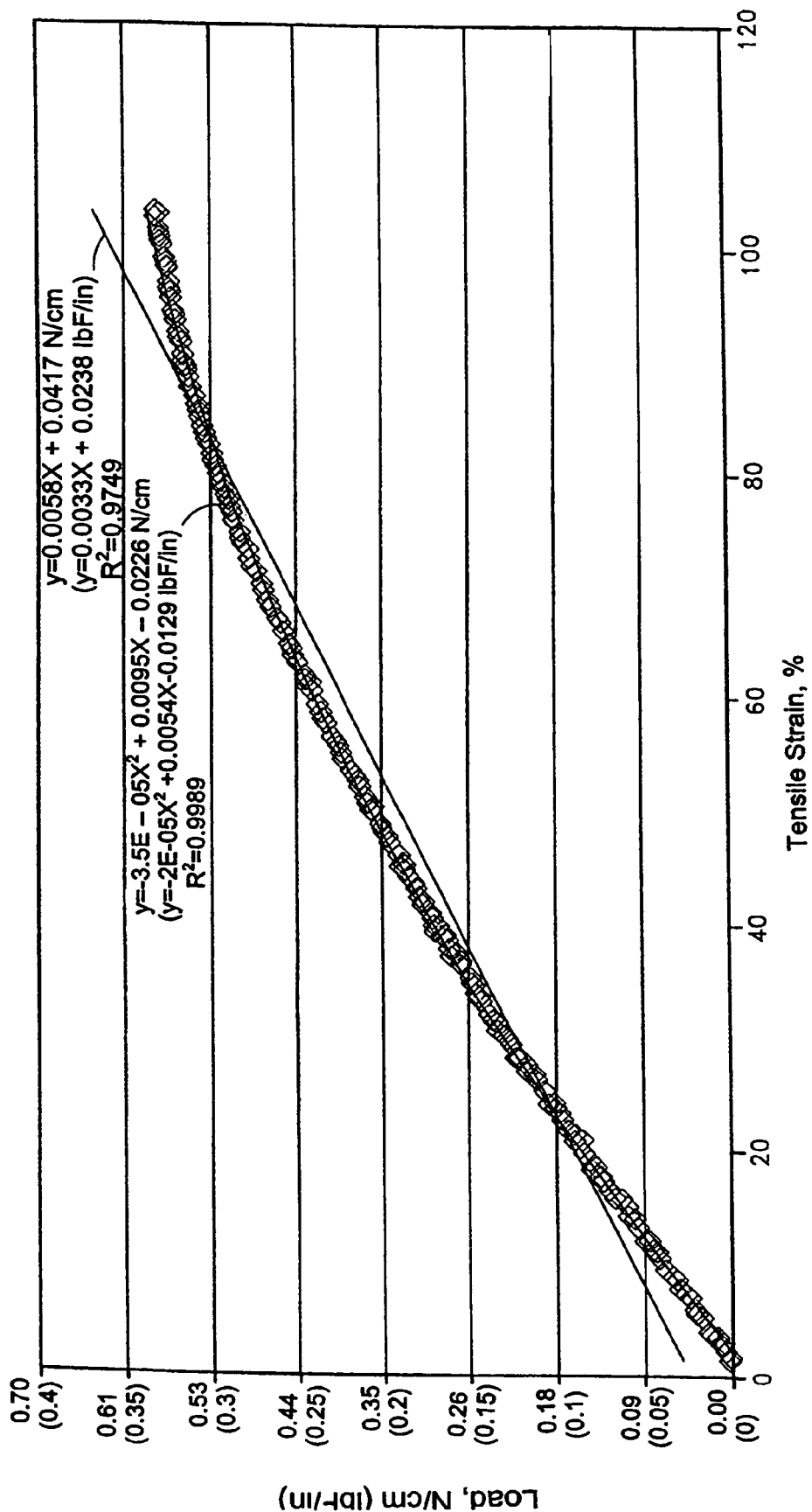
FIG. 18 shows test data and linear regression line derive therefrom for yet another embodiment of a cardiac harness.

With reference next to FIG. 18, plotted test data is presented for a test portion of another embodiment of a cardiac harness. The cardiac harness exemplified by the test data of FIG. 18 comprises strands of spring elements preferably formed of drawn Nitinol wire having a diameter of about 0.028 cm (0.011 in.). The spring elements resemble the spring element 34 shown in FIG. 14, and have a width w of about 0.419 cm (0.165 in.), a height h of about 0.414 cm (0.163 in.), and a diameter φ of about 0.320 cm (0.126 in.). After the wire is formed into strands of spring elements, it is heat treated at about 485° C. (905° F.) for about thirty minutes. Silicone tubing is disposed over the strand.

A test portion of the just-described cardiac harness was tested in a materials testing machine in accordance with the procedure discussed above. Test data, including load and percent tensile strain, was collected between a zero load, zero percent strain condition and about a one hundred percent strain condition. Representative test data points are set out in the plot of FIG. 18, in which percent strain is plotted along the x axis, and load, normalized with respect to the width W of the test portion, is plotted along the y axis.

With continued reference to FIG. 18, a linear regression of the test data was performed in order to derive a function describing the behavior of the cardiac harness in the form y=ax+b. The linear regression was performed using Microsoft™ Excel™ software, and yielded the function y=0.0058x+0.0417 N/cm (y=0.0033x+0.0238 lbF/in). The linear regression function has a coefficient of determination $R^2$ of about 0.9749.

With continued reference to FIG. 18, it is observed that the slope of the curve represented by the data points becomes lesser as the percent strain increases. A linear regression of the test data was performed in order to derive a function describing the behavior of the cardiac harness in the form y=ex$^2$+ ax+b. The linear regression was performed using Microsoft™ Excel™ software, and yielded the function y=−0.000035x$^2$+ 0.0095x−0.0226 N/cm (y=−0.00002x$^2$+0.0054x−0.0129 lbF/in.). This linear regression function has a coefficient of determination $R^2$ of about 0.9989.

Yet another embodiment of a cardiac harness comprises strands of spring elements formed of drawn Nitinol wire having a diameter of about 0.041 cm (0.016 in). The spring elements resemble the spring element shown in FIG. 14, and have a width w of about 0.734 cm (0.289 in.), a height h of about 0.699 cm (0.275 in.), and a diameter φ of about 0.635 cm (0.250 in). After the wire is formed into strands of spring elements, it is heat treated at about 515° C. (959° F.) for about twenty-five minutes. Silicone tubing is disposed over the strand.

A test portion of the just-described cardiac harness was tested in a materials testing machine in accordance with the procedure discussed above. Test data, including load and percent tensile strain, was collected between a zero load, zero percent strain condition and about a one hundred percent strain condition. A linear regression of the test data was performed in order to derive a function describing the behavior of the cardiac harness in the form y=ax+b. The linear regression was performed using Microsoft™ Excel™ software, and yielded the function y=0.005x+0.0128 N/cm (y=0.003x+ 0.0073 lbF/in.). The linear regression function has a coefficient of determination $R^2$ of about 0.9945.

In each of the embodiments discussed above, the compliance functions y=ax+b are determined based on test data between about zero percent strain and one hundred percent strain. It is anticipated that behavior of the harness test portions may change considerably if tested far beyond one hundred percent strain. However, it is to be understood that the tested range of expansion of about zero to one hundred percent represents a proposed operating range of expansion for each harness. In this operating range, the compliance behavior of the harness embodiments is known and predictable.

In accordance with one embodiment, the cardiac harness is sized and configured relative to a patient's heart so that the operating range of the harness is up to about seventy-five percent expansion. In another embodiment, the operating range of the harness is up to about fifty percent expansion. Although the tested embodiments have been tested only up to about one hundred percent expansion, it is to be understood that further testing may reveal acceptable behavior in ranges well above one hundred percent expansion. As such, an operating range of the harness should be taken to mean a range over which the compliance behavior of the harness is acceptable for its intended purpose of providing a mild compressive force to the patient's heart without defining a limit beyond which the heart cannot expand.

Further, it is to be understood that, by employing the compliance functions that are derived from the test data by linear regression, the compliance behavior of the associated harnesses can be predicted over any range of expansion or load. For example, with reference to the embodiment of FIG. 18, it can be determined that a change of about twenty percent in circumferential expansion within an operating range of expansion having a minimum value of at least twenty percent yields a change in circumferential load of about 0.116 N/cm (0.066 lbF/in.).

With reference to the embodiment of FIG. 15, it can be determined that a change of about twenty percent in circumferential expansion within an operating range of expansion between about zero and one hundred percent yields a change in circumferential load of about 0.035 N/cm (0.02 lbF/in.).

Experimental studies indicate that a cardiac harness having compliance properties as in the embodiment of FIG. 15 provide a beneficial therapeutic effect to a diseased heart. Studies also indicate that a cardiac harness having compliance properties as in the embodiment of FIG. 18 also provides a beneficial therapeutic effect. Preferably, however, a cardiac harness has compliance properties at or more compliant than the embodiment of FIG. 18. Thus, preferably a change of about twenty percent in circumferential expansion yields a change in circumferential load no greater than about 0.116 N/cm (0.066 lbF/in.).

As demonstrated by the several embodiments tested and discussed above, significant changes to the calculated compliance functions can be achieved by varying structural properties such as wire diameter, heat treatment, and dimensions of spring elements. It is anticipated that other cardiac harness embodiments can be constructed wherein a change of about twenty percent in circumferential expansion yields a change in circumferential load of about 0.116 N/cm (0.066 lbF/in), 0.035 N/cm (0.022 lbF/in), 0.032 N/cm (0.018 lbF/in), or any range between or below these values.

Testing harness embodiments as discussed above enables analysis of the behavior of the harness over its operating range. For example, the compliance function y=ax+b can be computed over the entire range of test data, as with the embodiments discussed above, or can be computed over only a selected range of test data. Pursuant to standard mathematical properties, the constant "a" represents the slope of the function.

With reference to the embodiment of FIG. 18, the slope of the test data declines as the percent expansion increases. As such, if a first slope "a" is calculated by linear regression over a first selected range of expansion, and a second slope "a" is calculated over a second selected range of expansion, which second range consists of expansion values greater than the first range, the second slope "a" will be less than the first slope "a." In other embodiments, such as that of FIG. 16, the second slope "a" will be nearly the same as, but no greater than the first slope "a" for at least portions of the test data. Preferably, each of the first and second ranges of data comprise a significant range of data, such as over at least five percent of expansion.

The analysis just discussed is helpful in analyzing cardiac harness compliance behavior to determine whether a cardiac harness exhibits desired behavior. For example, in a preferred embodiment, the second slope "a" is no greater than the first slope "a." It is further helpful to analyze such behavior over only portions of the range of expansion that are expected to be used during operation of the harness. For example, in another preferred embodiment, the second slope "a" is no greater than the first slope "a" within an operational range of expansion of the harness of about zero to one hundred percent expansion. In further preferred embodiments, the first selected range of expansion is within a range between about twenty and thirty percent expansion, and the second selected range of expansion is within a range between about twenty-five and one hundred percent expansion. In yet another embodiment, the second selected range of expansion is within a range between about twenty-five and fifty percent expansion.

In the embodiments discussed above, the compliance function has been defined by linear regression of test data taken over a percent expansion between about zero and one hundred percent. It is to be understood that such an analysis may also be helpful if taken over a more limited range of percent expansion. For example, the operating range of the harness may, in some embodiments, be limited to such a range of expansion. In accordance with one embodiment, the variation of load as a function of expansion between about twenty to thirty percent expansion is represent by the compliance function y=ax+b in which "a" and "b" are determined by linear regression, and wherein the value of "a" is no greater than about 0.0058 N/cm per percent expansion 0.0058 N/cm per percent expansion (0.0033 lbF/in per percent expansion).

In the illustrated embodiments, the coefficients of determination have been very close to 1. More particularly, the coefficients of determination are greater than about 0.9 band, in some embodiments, greater than about 0.98. Preferably, a compliance function determined by linear regression has a coefficient of determination of at least about 0.8 in order to be helpful for analysis as discussed herein.

For each of the analyses discussed above, characteristics over certain exemplary ranges of expansion have been specifically discussed. It is to be understood that, at least for the test data and corresponding compliance functions disclosed herein, the properties of the corresponding harnesses can be analyzed over any range of circumferential expansion or load. Such varying ranges of analysis are contemplated by the test data and the compliance functions. Such analyses are advantageous for defining the behavior of the corresponding harness embodiment.

Although this invention has been disclosed in the context of several preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A cardiac harness, comprising:
   a plurality of circumferentially extending rings formed from a metallic alloy;
   each ring having a plurality of non-overlapping spring members having a circumferential compliance and a longitudinal compliance, the circumferential compliance being greater than the longitudinal compliance; and
   a plurality of connectors for connecting adjacent rings, the connectors being formed from a non-metallic material.

2. The cardiac harness of claim 1, wherein the connectors define a space between adjacent rings.

3. The cardiac harness of claim 1, wherein the spring members are formed from a wire having a diameter of about 0.005 inch.

4. The cardiac harness of claim 1, wherein a circumferential load on the heart applied by the ring members during the cardiac cycle is in the range of about 0.0 N/cm (0.0 lb F/in.) to about 0.043 N/cm (0.025 lb F/in.) at an applied strain in the range of about 0.0% to about 20.0%.

5. The cardiac harness of claim 1, wherein the spring members are formed from a wire having a diameter of about 0.012 inch.

6. The cardiac harness of claim 5, wherein a circumferential load applied by the ring members during the cardiac cycle is in the range of about 0.0 N/cm (0.0 lb F/in.) to about 0.047 N/cm (0.026 lb F/in.) at an applied strain in the range of about 0.0% to about 20.0%.

7. The cardiac harness of claim 1, wherein the spring members are formed from a wire having a diameter of about 0.011 inch.

8. The cardiac harness of claim 7, wherein a circumferential load on the heart applied by the ring members during the cardiac cycle is in the range of about 0.0 N/cm (0.0 lb F/in.) to about 0.16 N/cm (0.09 lb F/in.) at an applied strain in the range of about 0.0% to about 20.0%.

9. The cardiac harness of claim 1, wherein the rings apply a continuous pressure on the heart in the range of about 2 mm Hg to about 20 mm Hg.

10. The cardiac harness of claim 1, wherein the rings apply a continuous pressure on the heart in the range of about 2 mm Hg to about 10 m Hg.

11. The cardiac harness of claim 1, wherein the rings apply a continuous pressure on the heart in the range of about 2 mm Hg to about 5m Hg.

12. A cardiac harness, comprising:
   a plurality of circumferentially extending rings formed from a nitinol alloy;
   each ring having a plurality of non-overlapping spring members having a circumferential compliance and a longitudinal compliance, the circumferential compliance being greater than the longitudinal compliance; and
   a plurality of connectors for connecting adjacent rings, the connectors being formed from a non-metallic material.

* * * * *